US008568984B2

(12) United States Patent
Su et al.

(10) Patent No.: US 8,568,984 B2
(45) Date of Patent: Oct. 29, 2013

(54) METHODS OF DIAGNOSING NON-URINARY TRACT DISEASES BY DETECTING ABERRANT METHYLATION

(75) Inventors: Ying-Hsiu Su, Audubon, PA (US);
Benjamin Song, Audubon, PA (US);
Janet Song, Audubon, PA (US);
Timothy M. Block, Doylestown, PA (US)

(73) Assignee: Philadelphia Health & Education Corporation, Philadelphia, PA (US)

( * ) Notice: Subject to any disclaimer, the term of this patent is extended or adjusted under 35 U.S.C. 154(b) by 123 days.

(21) Appl. No.: 13/030,888

(22) Filed: Feb. 18, 2011

(65) Prior Publication Data
US 2011/0207129 A1 Aug. 25, 2011

Related U.S. Application Data

(60) Provisional application No. 61/306,175, filed on Feb. 19, 2010.

(51) Int. Cl.
*C07H 21/04* (2006.01)
*C12Q 1/68* (2006.01)

(52) U.S. Cl.
USPC ....... 435/6.12; 435/6.11; 435/69.1; 536/23.1; 536/24.3

(58) Field of Classification Search
None
See application file for complete search history.

(56) References Cited

U.S. PATENT DOCUMENTS 7,112,404 B2 * 9/2006 Laird et al. .................. 435/91.2

OTHER PUBLICATIONS

Toyota et al. Cancer Research, vol. 59, pp. 4535-4541, Sep. 1999.*
Pao et al. (Human Molecular Genetics, vol. 10, No. 9, pp. 903-910) 2001.*
Cameron et al. (Blood, vol. 94, No. 7, pp. 2445-2451, Oct. 1999).*
Esteller et al. (Cancer Reserach, vol. 58, pp. 4515-4518, Oct. 1998).*
Baylin et al., "Alterations in DNA methylation: a fundamental aspect of neoplasia," Adv. Cancer Res., 1998, 72, 141-196.
Chen et al., "Detection in Fecal DNA of Colon Cancer—Specific Methylation of the Nonexpressed Vimentin Gene," Journal of the National Cancer Institute, Aug. 2005, 97(15), 1124-1132.
Eads et al., "MethyLight: a high-throughput assay to measure DNA methylation," Nucleic Acids Res., Apr. 15, 2000, 28(8), e32i—e32viii.
Perry et al., "The emerging roles of DNA methylation in the clinical management of prostate cancer," Endocr. Relat. Cancer, Jun. 2006, 13(2), 357-377.
Su et al., "Removal of high-molecular-weight DNA by carboxylated magnetic beads enhances the detection of mutated K-ras DNA in urine," Ann. N.Y. Acad. Sci., Aug. 2008, 1137 ed., 82-91.
Zou et al., "Highly Methylated Genes in Colorectal Neoplasia: Implications for Screening," Cancer Epidemiol Biomarkers Prev., Dec. 2007, 16(12), 2686-2696.

* cited by examiner

*Primary Examiner* — Jeanine A Goldberg
(74) *Attorney, Agent, or Firm* — Woodcock Washburn, LLP

(57) ABSTRACT

Provided are methods of diagnosing and/or determining treatment of non-urinary tract cancers by detecting biomarkers, and aberrant methylation in said biomarkers, in human urine samples.

1 Claim, 7 Drawing Sheets

Figure 2A

MSP - VIM57800_58211
                    INITIAL NUCLEOTIDE SEQUENCE
GCTGGGATGGCAGTGGGAGGGGACCCTCTTTCCTAACGGGGTTATAAAAACAGCGCCCTCGGCGGGGTCCAGTCCTC
TGCCACTCTCGTCCGAGGTCCCCGCGCCAGAGACGCAGCCGCGCTCCCACCACCCACACCCACCGCGCCCTCGTTC
GCCTCTTCTCCGGAGCCAGTCCGCGCCACCGCCGGCGCCCAGGGCATCGTCACCCTCCGCAGCCATGTCCACCAGG
TCCGTGTCCTCGTCCTCCTACCGCAGGATGTTCGGCGGCCGGGCACCGCGAGCCGCCGAGCTCAGCCGGAGCTA
CGTGACTACGTCCACCCGCACCTACAGCCTGGGCAGCGCGCTGGGCCCAGCACCAGCGCAGCCTCTACGCCTGGT
CCCCGGCGGCGTCTATGCCACGCG

SEQ ID NO: 11

Figure 2B   BISULFITE MODIFICATION OF DNA
GTTGGGATGGTAGTGGGAGGGGATTTTTTTTTTAACGGGGTTATAAAATAGCGTTTTCGGCGGGGTTT
AGTTTTTGTTATTTCGTTTGAGCGTTTTCGCGTTAGAGACGTAGTCGCGTTTTTATTATTTATATTTA
TCGCGTTTTCGTTCGTTTTTTTTCGGGAGTTAGTTCGCGTTATCGTCGTCGTTTAGGTTATCGTTATTT
TTCGTAGTTATGTTTATTAGGTTCGTGTTTTCGTTTTTTATCGTAGGATGTTCGGCGGTTCGGGTATCG
CGAGTCGGTCGAGTTTTAGTCGGAGTTACGTGATTACGTTTATTCGTATTTATAGTTTGGGTAGCGCGTT
GCGTTTTAGTATTAGTCGTAGTTTTTACGTTTCGTTTTCGGCGGCGTGTATGT 58341

SEQ ID NO: 12

Figure 2C    Figure 2D

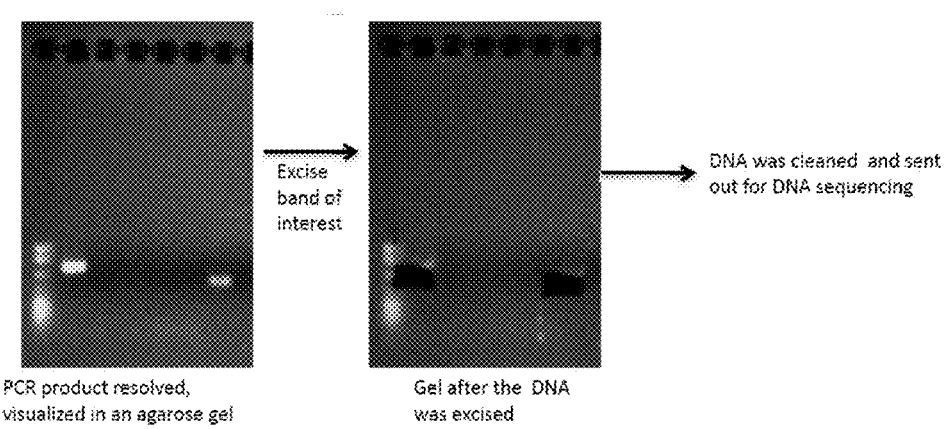

PCR product resolved,  Gel after the DNA
visualized in an agarose gel  was excised Excise band of interest DNA was cleaned and sent out for DNA sequencing

Figure 2E  Above dividing line: Bisulfite = SEQ ID NO: 13 ; WIDR = SEQ ID NO: 14
Below dividing line: Bisulfite = SEQ ID NO: 16 ; WIDR = SEQ ID NO: 16

Figure 3A

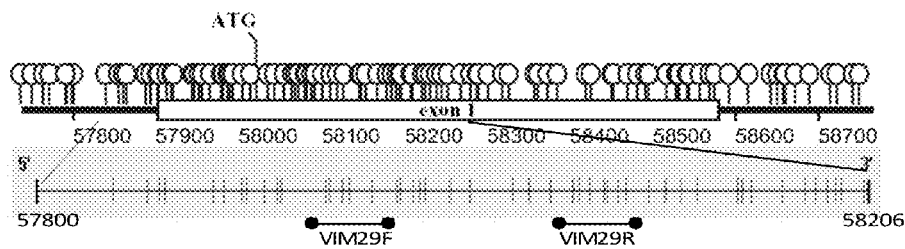

Figure 3B

```
57801
GTTGGGATGGTAGTGGGAGGGGATTTTTTTTTTTAACGGGGTTATAAAAATAGCGTTTTCGGCGGGGTTT
                                                        1F
                                                      1F1

57871
AGTTTTTTGTTATTTTCGTTTCGAGGTTTTCGCGTTAGAGACGTAGTCGCGTTTTATTATTTATATTTA
      1R   1R1          2R          3R
         VIM29F     VIM3F

57941
TCGCGTTTTCGTTCGTTTTTTTTTCGGGAGTTAGTTCGCGTTATCGTCGTCGTTTAGGTTATCGTTATTT
                                    4R
                   5R

58011
TTCGTAGTTATGTTTATTAGGTTCGTGTTTTCGTTTTTTTATCGTAGGATGTTCGGCGGTTCGGGTATCG
                                   2F1          2F
58081
CGAGTCGGTCGAGTTTTAGTCGGAGTTACGTGATTACGTTTATTCGTATTTATAGTTTGGGTAGCGCGTT
                          VIM29R       VIM29R1
```

SEQ ID NO:32

Figure 3C

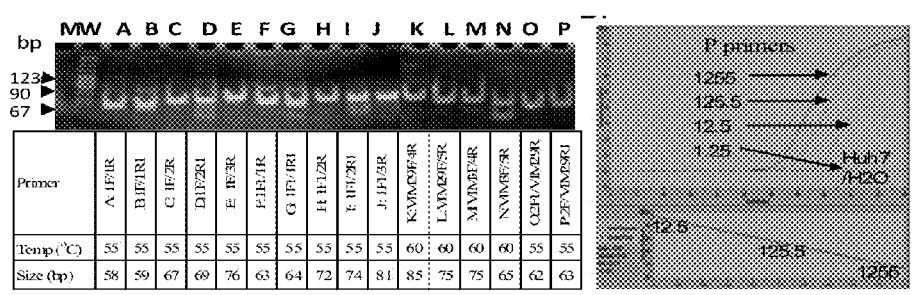

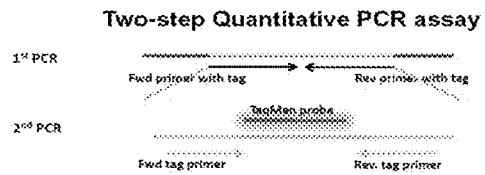

Figure 4C

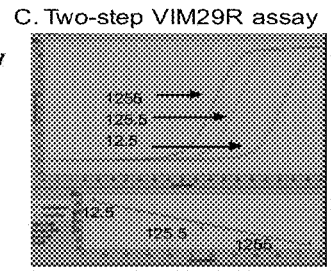

Figure 4B

VIM29F LNA probe: FAM-tttCgCgttagagaCg-BBQ1
VIM29F_sF:5'-tcgttcgaggtttcgc-3'
VIM29F_sFext:5'-tcgtggtggtgtcgttcgaggtttcgc-3'
VIM29F_sntF:5'-gtgtggtgtcgttcgag-3'
VIM29F_sRext:5'-cttcgtggtgtggtgaaaacgcgactacgtctc-3'
VIM29F_sntR:5'-tgtggtgaaaacgcgact-3'
VIM29F_ntR:5'-tggtgtggtgcgcgac-3'
*VIM29F_F:5'-gctcttcgtggtgtggtgttcgttcgaggtttcg-3'*
*VIM29F_R:5'-gctcttcgtggtgtggtgcgcgactacgtctctaa-3'*
*VIM29F_ntF:5'-gtgtggtgttcgttcgag-3'*
*VIM29F_ntR:5'-tcttcgtggtgtggtgc-3'*

VIM29R probe: FAM-atcgcgagtcggtcgagtt-BBQ1
VIM29R_ntR:5'-tggtgtggtgctccggac-3'
VIM29R_ntF1:5'-gtgtggtgcggttc-3'
VIM29R_ntR2:5'-gtgtggtgctccgac-3'
*VIM29R_F:5'-gctcttcgtggtgtggtgcggttcgggtatcgc-3'*
*VIM29R_R:5'-gctcttcgtggtgtggtgctccgactaaaactcgacc-3'*
*VIM29R_ntF:5'-tggtgtggtgcggttc-3'*
*VIM29R_ntR1:5'-tggtgtggtgctccga-3'*

SEQ ID NOS: 33-43, 9, 44-50, respectively, as read from top to bottom of first row, then second row

METHODS OF DIAGNOSING NON-URINARY TRACT DISEASES BY DETECTING ABERRANT METHYLATION

CROSS-REFERENCE TO RELATED APPLICATIONS

The present application claims priority to U.S. Provisional App. No. 61/306,175, filed Feb. 19, 2010, the entire contents of which are incorporated herein by reference.

GOVERNMENT RIGHTS

This invention was made with government support under Contract No. R01 CA125642 awarded by the National Institutes of Health-National Cancer Institute and Contract No. W81XWH-10-1-0042 awarded by the Department of Defense, United States Army Medical Research Acquisition Activity (USAMRAA). The government has certain rights in the invention.

SEQUENCE LISTING

The instant application contains a Sequence Listing which has been submitted in ASCII format via EFS-Web and is hereby incorporated by reference in its entirety. Said ASCII copy, created on Mar. 14, 2013, is named Sequence_Listing_CRF_DXBV-0028 and is 11,788 bytes in size.

TECHNICAL FIELD

The disclosures herein relate to biotechnology, particularly molecular biology and molecular detection of cancer.

BACKGROUND

Cancer is a leading cause of death worldwide: it accounted for 7.4 million deaths (around 13% of all deaths) in 2004. Deaths from cancer worldwide are projected to continue rising, with an estimated 12 million deaths in 2030.

Because cancer is a genetic disease, molecular changes, such as genetic and epigenetic DNA modifications, which result in neoplastic transformation, can be used as markers for the early detection of cancer.

Colorectal Cancer

Despite improvements in screening, colorectal cancer (CRC) remains the second leading cause of cancer death in the United States. When CRC is detected in its earliest stages, the survival rate can be as high as 90% compared with a survival rate of approximately 10% once the cancer has distantly metastasized. Currently, the recommended screening tests for CRC are colonoscopy or flexible sigmoidoscopy, but the adherence rate to take these tests is low (40%) in adults in the United States due to inconvenience, fear of discomfort, and the risks involved in invasive screening tests. The noninvasive fecal occult blood test (FOBT) is also available, but its sensitivity is low (30%). Another emerging noninvasive screening test for CRC is the stool genetic test. Although a high specificity (92%) was obtained in a well-defined screening study in an average-risk population, the sensitivity (52%) has not been satisfactory. Thus, U.S. Health Care authorities continue to recommend an invasive flexible sigmoidoscopy or colonoscopy every 10 years for average-risk adults despite the high cost and invasive nature of these tests.

Hepatocellular Carcinoma

Hepatocellular carcinoma (HCC) is the fifth most frequent cancer in the world, and is the third leading cause of cancer mortality, responsible for between 250,000 and 800,000 deaths per year. HCC is an aggressive malignancy with a poor prognosis with the 5 year survival rates are usually less than 5% following diagnosis using conventional methods of detection and treatment. However, early surgical and chemotherapeutic intervention can improve the prognosis, if early detection is possible. Unfortunately, the early stage of liver cancer is mostly asymptomatic, making the early detection of liver cancer a challenge. Current methods in detecting HCC include monitoring high risk groups such as those infected with HBV or HCV with regular (usually annual or biannual) physical assessments, serum liver function tests (LFTs), or ultrasound imaging for the detection of small masses in the liver. Ultrasound imaging is very expensive, making its routine use prohibitive. Moreover, detection requires the appearance of masses of at least 3 cm in size, and the outcome of the prognosis at that size is very poor. In addition to imaging techniques, the detection of the elevated serum concentrations of alpha-feto protein (AFP) has provided a useful surrogate marker for disease with at least 60% of the cases of HCC having the elevated AFP level at the time of diagnosis. However, the elevated level of AFP is influenced by and can occur because of a number of other non-malignant physiological events. It is nearly impossible to detect HCC early using current methods of detection. Thus, there is a clear and urgent need for non-invasive, reliable methods for the early detection of HCC.

Success in the treatment of individuals with cancer, such as CRC or HCC, often depends upon early detection. The earlier a tumor is detected, the better the prognosis. Many of the 520,000 lives lost to cancer each year could be saved with early detection. In many pre-neoplastic conditions, such as an inherited predisposition to a specific tumor type or in a disease-promoting neoplastic transformation, high risk individuals could be identified, and early detection programs could be implemented. From the patient's point of view, a diagnostic test is less unpleasant, invasive, and expensive, and is also more likely to be used. The importance of a non-invasive diagnosis for early cancer detection can be illustrated by the colorectal cancer screening test. These tests such as rectocolonoscopy and sigmoidoscopy are effective in detecting CRC early. Unfortunately, the low compliance rate (25-35%) of adults in the US has been a problem due to inconvenience, fear of discomfort, and the risk involved in the screening test. Thus, a noninvasive, effective screening method is needed to improve a patient's comfort, so that the compliance rate can be increased, and cancer can be detected early. In all, more work is needed to develop a noninvasive, less unpleasant, highly sensitive, and less expensive screening test to augment adherence rates and to increase the role of early detection in disease prognosis.

SUMMARY

Urine has been used as a source of reporter molecules for urinary tract diseases with great clinical benefit. Urine-based tests are non-invasive and very patient-friendly. The advances in molecular biomarker assays and recent findings that tumor-derived DNA in the circulation less than 300 bp in size can be detected in urine as low MW urine DNA have provided the possibility for the use of urine as the biological fluid for cancer detection. A high-throughput technology to preferentially isolate this low MW urine DNA species was developed. It has been shown that as compared to using total urine DNA, using low MW urine DNA as the substrate enhanced the sensitivity and specificity to detect tumor-derived genetic mutations in urine. However, it was unknown whether urine DNA or low MW urine DNA could be successfully used to detect epigenetic changes that occurred elsewhere in the body. Herein is described technology suitable for the use of urine as a body fluid to detect epigenetic changes cancer-associated DNA markers for the early detection of liver and/or colon cancer and/or other non-urinary tract diseases.

Disclosed herein are methods for diagnosing a non-urinary tract disease in a subject comprising detecting aberrant methylation of DNA in urine of the subject, and correlating the detected aberrant methylation to the absence or presence of the disease. DNA that is "in" the urine of the subject refers to DNA that is present within the urine of the subject or DNA that was formerly present within the urine of the subject but was subsequently isolated from the urine. The present methods may therefore involve isolating the DNA from the urine prior to detecting aberrant methylation.

The disease may be precancer or cancer. For example, the disease may be an adenoma, colon cancer, or liver cancer.

The DNA may be low molecular weight DNA. In some embodiments, the low molecular weight DNA is isolated from the urine, for example, by use of magnetic beads.

The present methods further comprise detecting one or more organ specific markers, one or more molecular markers that are specific to or can identify a particular organ, or both, from among the DNA. For example, a plurality of organ-specific markers, a panel of molecular markers, or both may be detected from among the DNA. The methods may also or alternatively comprise detecting one or more drug resistance markers from among the DNA. For example, the drug resistance marker may be indicative of resistance to a chemotherapy drug.

The instant methods may comprise performing a two step methyl-specific PCR assay to detect aberrant methylation. The PCR assay may be a real-time PCR. An LNA primer may be used in the PCR assay.

Also disclosed herein are methods for identifying a chemotherapeutic for treatment of a non-urinary tract disease comprising detecting one or more biomarkers identified as correlating with efficacy of said chemotherapeutic in the treatment of said non-urinary tract disease.

Also provided are kits for use in diagnosing a non-urinary tract disease. In one embodiment, the kit comprises reagents for detecting aberrant methylation in a sample of human urine.

The present invention also pertains to controls for real time PCR assays to specifically detect actin in a sample containing bisulfite treated DNA. In one embodiment is a method performing real time PCR to detect bisulfate converted actin DNA wherein the forward primer is an oligonucleoide comprising the sequence of GATGTATGAAGGTTTTTGG (SEQ ID NO: 1) and the reverse primer is an oligonucleotide comprising the sequence of CTAACTACCTCCACCCACTC (SEQ ID NO: 2). In yet a further embodiment, the forward primer is the oligonucleoide consisting of GATGTATGAAG-GTTTTTGG (SEQ ID NO: 1) and the reverse primer is the oligonucleotide consisting of CTAACTACCTCCAC-CCACTC (SEQ ID NO: 2).

The kits and methods above permit detection of epigenetic, genetic, miRNAs, aberrant methylation, and gene expression in one assay.

BRIEF DESCRIPTION OF THE DRAWINGS

FIG. 2A (SEQ ID NO: 11) depicts the nucleotide sequence of the vimentin gene from nt 57800 to nt. 58211 (Genebank Accession # AL133415).

FIG. 2B (SEQ ID NO: 12) depicts the converted bisulfite treated DNA sequences as predicted by the Methyl Primer Express software.

FIG. 2C is an image of an electorphoretic agarose gel resolving PCR products amplified by bisulfite sequencing primers analyzed and visualized using ethidium bromide staining FIG. 2D is an image of the agarose gel after excision of the PCR bands.

FIG. 2E (SEQ ID NOS 13-16) depicts and alignment of the empirically determined DNA sequencing data to the sequence predicted by Methyl Primer Express using Clustal software.

FIG. 3A is a schematic showing exon 1 of the VIM gene, the ocation of CpG methylation sites, and the location where the forward and reverse primers (VIM29) anneal to the gene. Each circle or vertical line represents a CpG site.

FIG. 3B (SEQ ID NO: 32) is a schematic showing exon 1 of the VIM gene and the location where the designed forward and reverse primer sets anneal to the VIM gene sequence.

FIG. 3C is an image of an electrophoretic agarose gel resolving the PCR bands of 18 different primer sets designed to amplify various fragments of the VIM gene.

FIG. 3D depicts the amplification and standard curves of primer P using reconstituted (spiked) control standard template demonstrating an assay sensitivity of 12.5 copies per reaction.

FIG. 4A is a schematic diagram of a two-step PCR assay, showing that the forward and reverse primers of the $1^{st}$ PCR include sequences that anneal to the template sequence and also include irrelevant artificial tag sequences that do not anneal to the template. After 10-20 cycles of the $1^{st}$ PCR assay, the $2^{nd}$ PCR detects the amplification product of the $1^{st}$ PCR assay using a second set of primers, forward and reverse primers that anneal to the amplified tag sequences, and a TaqMan probe specific to the target DNA template sequence.

FIG. 4B (SEQ ID NOS: 33-43, 9, 44-50, respectively) depicts the designed probe and primer sequences for two-step PCR assay development. The capitalized letters indicate the sites of LNA molecules.

FIG. 4C depicts the amplification and standard curves generated from a reconstituted standard mVIM by the two-step nested VIM29R PCR assay. The bottom panel shows the amplification curve and a linear standard of the assay detecting the mVIM in serial 10-fold dilutions (10, 100, and 1000 copies as indicated) of the bisulfite-treated positive control WiDr DNA.

DETAILED DESCRIPTION OF ILLUSTRATIVE EMBODIMENTS

Figures 1A, 1B:
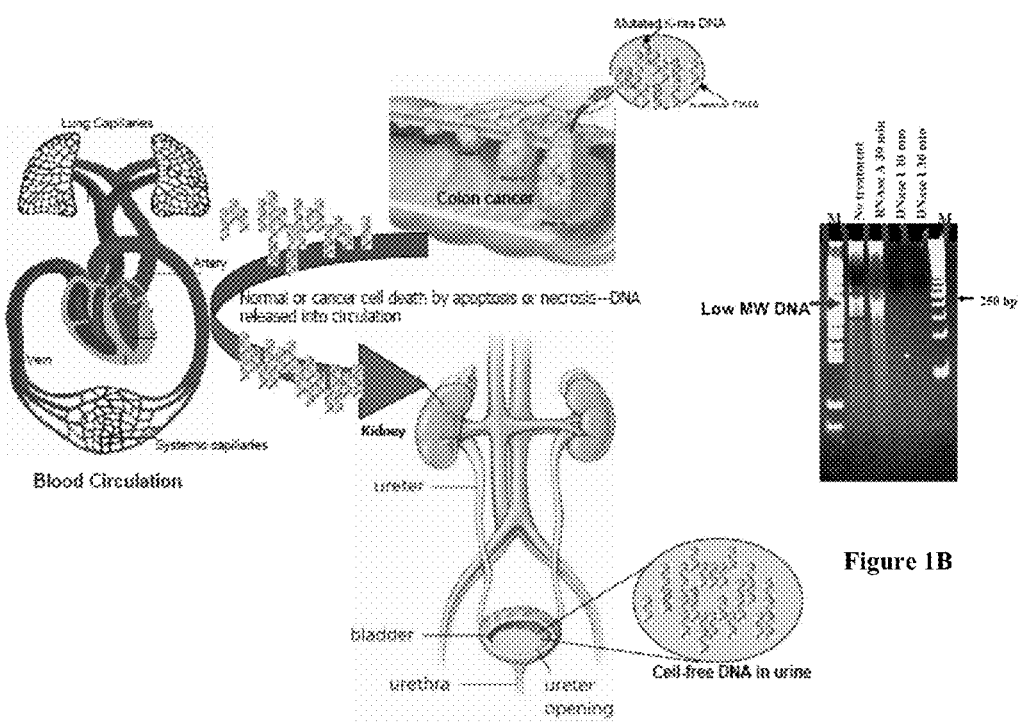
FIG. 1A is a schematic illustration of the mechanism that generates circulation-derived DNA in urine.
FIG. 1B is an image of a polyacrilamide gel resolving DNA isolated from CRC tissue (AAt), adjacent normal tissue (AAadj), serum (AAs) and urine (AAu) from CRC patient AA and urine (Zu) from healthy control that was subjected to the RE-PCR assay for the detection of K-ras condon 12 mutation and digested with BstNI. The 71 bp fragment corresponds to mutated K-ras DNA.

The present inventions may be understood more readily by reference to the following detailed description taken in connection with the accompanying figures and examples, which form a part of this disclosure. It is to be understood that these inventions are not limited to the specific products, methods, conditions or parameters described and/or shown herein, and that the terminology used herein is for the purpose of describing particular embodiments by way of example only and is not intended to be limiting of the claimed inventions.

It is intended that any component, element, attribute, or step that is positively recited herein may be explicitly excluded in the claims, whether such components, elements, attributes, or steps are listed as alternatives or whether they are recited in isolation.

In the present disclosure the singular forms "a," "an," and "the" include the plural reference, and reference to a particular numerical value includes at least that particular value, unless the context clearly indicates otherwise. Thus, for example, a reference to "a reagent" is a reference to one or more of such reagents and equivalents thereof known to those skilled in the art, and so forth. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive; as another example, the phrase "about 8%" preferably (but not always) refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", "2-5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." It is intended that any component, element, attribute, or step that is positively recited herein may be explicitly excluded in the claims, whether such components, elements, attributes, or steps are listed as alternatives or whether they are recited in isolation.

The disclosures of each patent, patent application, and publication cited or described in this document are hereby incorporated herein by reference, in their entirety.

The term "disease" or "disorder" is used interchangeably herein, and refers to any alteration in state of the body or of some of the organs, interrupting or disturbing the performance of the functions and/or causing symptoms such as discomfort, dysfunction, distress, or even death to the person afflicted or those in contact with a person. A disease or disorder can also relate to a distemper, ailing, ailment, malady, disorder, sickness, illness, complaint, inderdisposion, or affectation.

A "non-urinary tract" disorder or disease or cancer is one that is not primarily associated with an alteration of the bladder, urinary tract, kidney, renal, or the like. A "non-urinary tract" disorder or disease or cancer also excludes those that are primarily associated with an alteration of the prostate. Without wishing to be bound by any particular theory, a "non-urinary tract" disorder or disease or cancer generally involves organs that are distal to or do not function as part of the urinary tract, such as, but not limited to, the colon or liver.

As used herein, "cancer" refers to any stage of abnormal growth or migration of cells or tissue, including precancerous cells or tissue. "Precancer" refers to all stages of cancerous cells, including but not limited to adenomas, metaplasias, heteroplasias, dysplasias, neoplasias, hyperplasias, or anaplasias.

As used herein, "cancer progression" refers to any measure of cancer growth, development, and/or maturation including metastasis. "Cancer progression" includes increase in cell number, cell size, tumor size, and number of tumors, as well as morphological and other cellular and molecular changes and other characteristics. As an example, one measure of cancer progression is the use of staging characteristics. As an additional example, one measure of cancer progression is the use of detecting expression, whether at the protein or mRNA level, of certain genes The term "agent" refers to any entity which is normally not present or not present at the levels being administered in the cell. Agent can be selected from a group comprising: chemicals; small molecules; nucleic acid sequences; nucleic acid analogues; proteins; peptides; aptamers; antibodies; or fragments thereof. A nucleic acid sequence can be RNA or DNA, and can be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA) etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc. A protein and/or peptide or fragment thereof can be any protein of interest, for example, but not limited to: mutated proteins; therapeutic proteins and truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. Alternatively, the agent can be intracellular within the cell as a result of introduction of a nucleic acid sequence into the cell and its transcription resulting in the production of the nucleic acid and/or protein inhibitor of a protein or receptor or other molecule within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

As used herein, the term "chemotherapeutic" refers to cytotoxic, cytostatic, and antineoplastic agents that preferentially kill, inhibit the growth of, or inhibit the metastasis of neoplastic cells or disrupt the cell cycle of rapidly proliferating cells. Chemotherapeutics include, but are not limited to, synthetic compounds, natural and recombinant bacterial toxins, natural and recombinant fungal toxins, natural and recombinant plant toxins, and other agents. Specific chemotherapeutics are known in the art.

The term "drug resistance" refers to the reduction in effectiveness of a drug, such as an agent or a chemotherapeutic, in curing a disease or improving a patient's symptoms. It also refers to drug tolerance. Diseased cells, such as pre-cancerous or cancerous cells, are considered to be drug-resistant when drugs meant to neutralize them have a reduced and/or negated effect. When a diseased cell is resistant to more than one drug, it is said to be multidrug resistant.

The term "diagnosing" means any method, determination, or indication that an abnormal or disease condition or phenotype is present. Diagnosing includes detecting the presence or absence of an abnormal or disease condition, and can be qualitative or quantitative.

"Gene" is well known in the art, and herein includes, inter alia, non-coding region such as promoter or other regulatory sequences or proximal non-coding region.

The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression/production of an antibody or antigen-binding fragment can be within the cytoplasm of the cell, and/or into the extracellular milieu such as the growth medium of a cell culture.

The term "biomarker" is an agent used as an indicator of a biological state. It can be a characteristic that is objectively measured and evaluated as an indicator of normal biological processes, pathogenic processes, or pharmacologic responses to a therapeutic intervention. A biomarker can be a fragment of genomic DNA sequence that causes disease or is associated with susceptibility to disease, and may or may not comprise a gene.

Biomarkers and Aberrant Methylation

Typically, molecular changes in cancer cells lead to altered gene expression patterns that can be identified long before the cancer phenotype has manifested at the cellular level. The molecular changes can be genetic or epigenetic. When compared to normal cells or tissues, these changes that occur in the cancer cell can be used as biomarkers. DNA biomarkers comprise DNA in cells, such as mutations or changes in methylation. Changes in methylation are called "aberrant methylation," and may be hypomethylation or hypermethylation or an alteration of methylation of a gene as compared to a wild-type or non-disease or disorder or cancer-associated gene.

Human Urine Samples

The use of circulating DNA in plasma and serum for the early detection of cancer has been studied. Studies have demonstrated that urine contains DNA from circulation. FIG. 1A is a schematic illustration of the mechanism that generates circulation-derived DNA in urine. Urine contains DNA in fractions that fall within one of two general size ranges. One fraction is small (150 to 250 bp) cell-free, nucleosome-sized DNA fragments, which is designated as "low-molecular-weight (MW) urine DNA." Low MW DNA derives mostly from circulation. In contrast, large (1,000+ bp), cell-associated DNA derives from the urinary tract; cancers of the bladder, kidney and prostate contribute cellular DNA to urinary sediment (Perry A S, et al. Endocr Relat Cancer. 2006 June; 13(2):357-77.). The isolation of low-MW urine DNA can be accomplished by a number of methods known in the art, such as fractionation of total urine DNA through agarose gel electrophoresis and solid-phase carboxylated magnetic beads (CMBs), as described in Su Y-H, et al., Ann N Y Acad. Sci., 2008 August, 1137: 82-91.

It is to be understood that the embodiments described herein are not limited to particular methods, reagents, compounds, compositions or biological systems, which can, of course, vary. It is also to be understood that the terminology used herein is for the purpose of describing and is not intended to be limiting.

Exemplary Methodologies

1. Use of Urine DNA to Detect CRC-associated K-ras Mutation

FIG. 1A shows a schematic demonstrating the likely origins of circulation-derived urine DNA, which is fragmented, less than 300 by in size, and designated as low molecular weight (MW) urine DNA. FIG. 1A also depicts that this low MW urine DNA can be used for detecting cancer-derived genetic mutations. FIG. 1B shows an electrophoretic gel of CRC-associated K-ras mutations as assessed in DNA isolated from diseased tissue, adjacent normal control tissue, serum, and urine. The results demonstrate that mutated K-ras DNA was detected in CRC tissue, as indicated by the appearance of the 71 bp DNA fragment after BstNI digestion, but was not detected in adjacent normal tissue. These mutated sequences were verified by sequencing DNA isolated from the serum and urine samples.

Recent studies also suggested that the concentration of circulating DNA in urine is similar to that in plasma or serum. CRC-derived mutated K-ras DNA was detected more frequently in urine as compared to serum or plasma as described in Su Y-H, et al., Ann N Y Acad. Sci., 2008 August, 1137: 82-91, which is hereby incorporated by reference in its entirety. This demonstrates that urine is a good source for circulating DNA and can be used as the substrate for detecting circulation derived DNA markers.

2. Human Patient and Collection of Urine Samples Containing Low MW DNA

Subjects were recruited from the Great Lakes-New England Clinical Epidemiological Center under IRB approval. Cancer patients were enrolled from surgical or oncologic services prior to treatment, and controls with "no known neoplasia" were enrolled from endoscopy suites where they had undergone negative colonoscopies. Patients were matched for age and gender when possible.

Patient urine samples, obtained under institutional IRB approval, were processed prior to this study for total urine DNA. Each patient sample was given a random and unique code for the blinded study, and patient identity was kept private. Diagnostic information was unblinded after experimentation for analysis without revealing patient identity.

3. Fractionation of Low Molecular Weight (Low MW) DNA

The low MW urine DNA fraction of urine was obtained using carboxylated magnetic beads (Agentcourt Bioscience Corporation, Beverly, Mass.) and the binding method described in Su Y-H, et al, "Removal of high molecular weight DNA by carboxylated magnetic beads enhances the detection of mutated K-ras DNA in urine," 1137 ed., 2008. p. 82-91., hereby incorporated by reference in its entirety.

4. Bisulfite Treatment of DNA

Methylation of CpG sites can be detected by DNA sequencing or methylation specific PCR after bisulfite treatment, which converts unmethylated cytosine to uracil while retaining methylated cytosine as cytosine. Here, Qiagen Epitect Bisulfite conversion kits (Qiagen, CA) and Zymo Research EZ DNA Methylation Gold kits (Zymo Research, Zymo Research Corporation, CA) were used according to the manufacturer's specifications for bisulfite conversion.

5. DNA Quantification by Real-time Polymerase Chain Reaction (PCR)

DNA was quantified by real-time PCR using the LightCycler PCR instrument (Roche Biochemical, Germany) and the LightCycler-Faststart DNA master SYBR Green kit (Roche Biochemical, Germany) according to the manufacturer's specification. Primers for the albumin gene (forward, 5'-ccgtggtcctgaaccagtta-3'(SEQ ID NO: 3); reverse, 5'-gtcgc-ctgttcaccaaggat-3'(SEQ ID NO: 4) and serially diluted genomic DNA as quantification standards were used to quantify the total DNA. To quantify the bisulfite converted DNA, actin primers (forward, 5'-gatgtatgaaggtttttgg-3'(SEQ ID NO: 1), reverse, 5'-ctaactacctccacccactc-3'(SEQ ID NO: 2)) within the regions that did not have any CpG sites in the gene, were chosen so that the degree of CpG methylation did not affect the primer binding.

6. Validation of Methyl Primer Express Software

In order to facilitate the methylation specific PCR assay design, Methyl Primer Express by Applied Biosystems software was used to generate DNA sequences after bisulfite treatment and primer design. First, the Methyl Primer Express software was validated by evaluating the accuracy of the software and relevance of the analysis to a real sample by using DNA isolated from WiDr, a mVIM-positive cell line. DNA sequences from the promoter and the first exon regions of the vimentin gene were obtained from Genbank (Accession number AL133415), as shown in FIG. 2A, and entered into the Methyl Primer Express software for analysis. The software converted the sequences into predicted bisulfite-treated sequences, which are shown in FIG. 2B. DNA isolated from WiDr cells were treated by the Qiagen Epitect bisulfite kit according to the manufacturers directions, subjected to PCR amplification using bisulfite sequencing primers described in Zou H, et al., Cancer Epidemiol Biomarkers Prev, 2007 Dec. 1, 16(12):2686-96, which is hereby incorporated by reference in its entirety, and then excised after gel electrophoresis (FIGS. 2C, 2D). The excised agarose slices were purified using the Qiagen Gel Extraction kit according to the manufacturer's specifications and sequenced. DNA sequencing data (WIDR_Seq_F-VIMSeqq1051F) was compared to the sequence generated by the Methyl Primer Express software (FIG. 2E).

As seen in the comparison in FIG. 2E, the sequence generated from the DNA sequencing reaction of bisulfite-treated WiDr DNA was highly consistent (>99% identity) with the bisulfite-converted sequence generated by the Methyl Primer Express software using DNA sequences imported from GenBank, validating the Methyl Primer Express software. Therefore, the Methyl Primer Express software was used to design methylation-specific primers for mVIM.

7. Development of One-Step MSP Assays for mVIM

In order to target the shorter sized template while retaining specificity for VIM29, assays were designed for each primer region, as indicated in FIG. 3A. Methyl Primer Express was used to assist in MSP primer design. Multiple primers were designed and tested. The sequences of each designed primer and its position in the gene are listed in FIG. 3B. The primer sets, tested annealing temperatures for PCR amplification, and the anticipated size of PCR products for each proposed pair are listed in FIG. 3C. Each primer was tested using bisulfite-treated WiDr DNA for its priming specificity with 40 cycles of PCR. PCR products were analyzed in 10% polyacrylamide gels (FIG. 3C). The primer sets were further tested for efficacy and specificity under the real-time PCR conditions (data not shown). The P primer set targeting VIM29R was successfully optimized to have a sensitivity of 12.5 copies per reaction as shown in FIG. 3D.

8. Development of PCR Assays for the Aberrant Methylation of the Vimentin Gene

There are several known assays developed for the detection of CRC-associated methylation DNA markers, however, none of these assays are designed for short DNA substrates of less than 300 bp, such as those found in urine. A CRC biomarker that is aberrantly hypermethylated, the vimentin (mVIM) gene, was used to develop an assay to detect the short target template DNA in urine.

It has been suggested that not all CpG site methylations are associated with CRC tumorgenesis. A comprehensive study utilizing ten different primer sets covering the promoter and first exon region of the vimentin gene was performed to map CRC-related methylations of the vimentin gene as described in Chen W D, et al., Gene. J Natl Cancer Inst, 2005 Aug. 3, 97(15):1124-32, which is hereby incorporated by reference in its entirety. Among these 10 tested primers, MSP29 had the best specificity and sensitivity for CRC.

Thus, assays targeting the primer regions of MSP29 (designated as VIM29F and VIM29R in FIG. 2A) were developed to detect mVIM in the urine of patients with CRC to test our hypotheses in a blinded study. Using the assay, CRC-associated aberrant hypermethylation markers were detected in urine with a higher sensitivity and specificity than detection using a CRC screening test (FOBT), the only other known noninvasive screening test.

Target sequences from the promoter and first exon region of the vimentin gene were obtained from GenBank (accession #AL133415) using NCBI PubMed software, and CpG analysis was performed using Methyl Primer Express software (Applied Biosystems, CA) after the method was verified. Primers and probes for one-step methylation specific PCR (MSP) assays targeting template sizes from 60-100 bp (listed in FIG. 3B) or two-step nested MSP assays targeting template sizes around 40 bp (listed in FIG. 4B) were designed and performed using the LightCycler PCR instrument (Roche Biochemical, Germany) according to the manufacturer's specification.

For two-step nested PCR assays, the first PCR reaction was performed in a thermocycler (Eppendorf, Germany) using the first PCR primer set (0.1 µM), dNTP (20 µM), and Hotstart Taq (Qiagen) at an annealing temperature of 60° C. for 30 cycles. The first PCR primer set incorporated with locked nucleic acid (LNA) (forward 5'-gctcttcgtggtgtggtgcggttcggg-tatcgc-3' (SEQ ID NO: 5), reverse 5'-gctcttcgtggtgtggtgctc-cGactaaaactcGacc-3' (SEQ ID NO: 6); note, LNA molecules are capitalized) was used in later experiments. The second PCR was performed using the LightCycler PCR instrument with the second PCR primer set (0.5µM) (VIM29R2F1: 5'-gt-gtggtgcggttc-3' (SEQ ID NO: 7), VIM29R2R2: 5'-gtgtggt-gctccgac-3' (SEQ ID NO: 8) and the probe (VIM29Rs probe: FAM-atcgcgagtcggtcgagtt-BHQ1 (SEQ ID NO: 9)) (0.15 µM) with Roche Lightcycler TaqMan 5× master mix at an annealing temperature of 60° C. for 40 cycles.

9. Sensitivity and Specificity of mVIM Assays

To determine the sensitivity of each assay, reconstituted standard samples ranging from 0.25 to 1255 copies of WiDr DNA (positive control for mVIM) per 100 ng/µl of HepG2 DNA (negative control for mVIM) were used to assess assay sensitivity. The range of linearity of the assay was determined. To determine the specificity of the assays, five cell lines, WiDr (mVIM-positive CRC cell line), SW480 (mVIM-negative CRC cell line), HepG2 (mVIM-negative non-CRC cell line), Hela (mVIM-negative non-CRC cell line), and Huh7 (mVIM-negative non-CRC cell line), were used.

10. Development of Two-Step Nested MSP Assay for mVIM

In order to design an assay with a target template size of about 40 bp or less, three approaches were used, as illustrated in FIG. 4A. First, a DNA primer containing an extraneous, non-annealing tag sequence was used in the initial PCR to increase the amplicon size. Second, primers that annealed to the tag sequence were used in the second PCR reaction. Third, since the $T_m$ of the TaqMan probe must be 5-10° C. higher than that of the primers for the second real-time PCR, locked nucleic acids (LNA) were incorporated to allow for a shorter probe, as indicated in FIG. 4B. Two-step PCR assays were designed for VIM29F and VIM29R as regions indicated in FIG. 3A. More than one set of primers, as listed in FIG. 4B, were designed to ensure the success of assay development. The assay development for the two-step PCR included optimization of the $1^{st}$ PCR conditions and the $2^{nd}$ PCR conditions using the PCR product generated from the $1^{st}$ PCR in a LightCycler (Roche) real-time PCR platform. Two two-step nested PCR for VIM29R and VIM29F were successfully developed with a sensitivity of 12.5 copies as an example shown for VIM29R in FIG. 4C.

11. Selection of a Kit for Bisulfite Treatment

Bisulfite treatment followed by DNA sequencing or MSP is used to distinguish methylated sequences from unmethylated sequences. However, DNA is often damaged during this conversion because it is performed at a pH of 5 for more than five hours and the recovery rate is less than 10%. The quantity of circulation-derived urine DNA is limited and the DNA of interest in urine is in an even smaller fraction so an efficient method with a high DNA recovery rate is needed. There are several commercial kits available for bisulfite treatment. Based on DNA sequencing data from the Methyl Primer Express validation study, the bisulfite conversion by Qiagen kit was very efficient. Another commonly used bisufilte conversion kit from Zymo Research was chosen for comparison. To compare the two commercial bisulfite kits for their efficiency in converting C to U and the rate of DNA recovery, similar amounts of WiDr DNA were used to test each kit.

Figure 5:
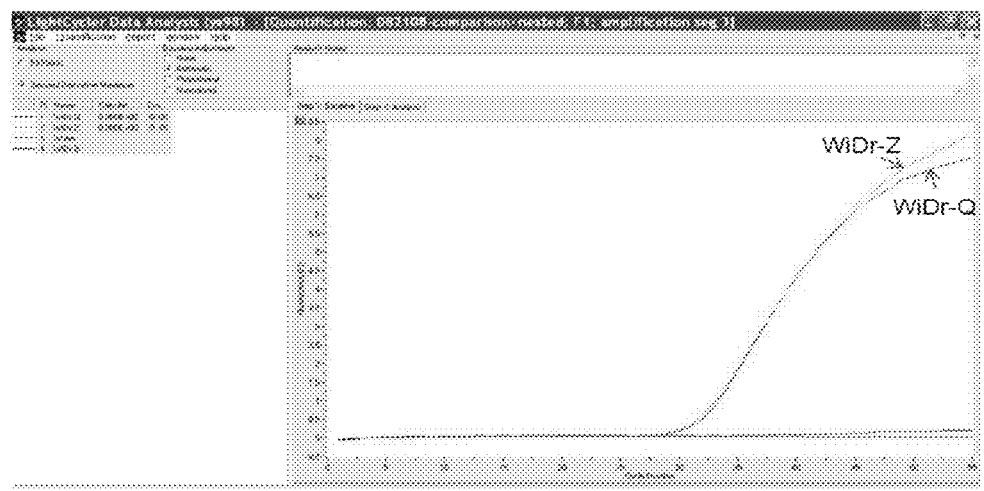
FIG. 5 is an image of the PCR amplification curves using the vimentin primer set P for 40 cycles and 500 ng of WiDr DNA subjected to bisulfite conversion by either the Qiagen (Q) kit or the Zymo Research (Z) kit according to the manufacturers' specifications. (DNA was eluted in 50 ul of $H_2O$ from each kit (WiDr Q and WiDr Z). 1 μl from a 1:10 dilution of eluted DNA was used for PCR)

As shown in FIG. 5, the crossing points of the amplification curves for WiDr Q and WiDr Z are 32.00 cycles and 31.78 cycles respectively. For an efficient real-time PCR amplification, a 10-fold difference in DNA quantity exhibits approximately a 3.34 cycle difference. There was only a 0.22 cycle difference suggesting only a 6% difference in quantification between these two independently processed samples. This small difference suggests that the efficiency of conversion and the recovery rate are similar for these two kits. Although the Zymo Research kit required less time (3 h), the Qiagen kit provided more secure mechanical connections between each step, so the Qiagen kit was chosen for processing the clinical urine specimen and the control cells for the following experiments.

12. Specificity of CpG Sites/Clusters to CRC as Determined Using CRC Cell Lines

It is well known that in addition to carcinogenesis, methylation can be associated with other processes such as aging. It is also known that not all methylated CpG sites in the promoter and first exon regions of the vimentin gene are specific to colon cancer carcinogenesis. To test the specificity of the clusters of CpG sites that were chosen for assay development for CRC, DNA isolated from five different cell lines, HeLa, Huh7, HepG2, WiDr, and SW480 were subjected to bisulfite treatment using the Qiagen Epitect kit and then subjected to both one-step (P) and two-step nested (VIM29F and VIM29R) MSP assays. It was found that the hypermethylation of the CpG sites in the VIM29R (P and VIM29R) region occurs specifically in CRC. The methylation of CpG sites in the VIM29F region is not specific for CRC, as all five cell lines tested are positive (data not shown).

13. Detection of Hypermethylated Vimentin in Low MW Urine DNA

In order to test the suitability of the developed assay for low MW urine DNA and determine whether a smaller target template size would exhibit higher sensitivity, low MW urine DNA from 10 normal subjects and 10 patients with colorectal cancers were tested. Low MW urine DNA was first subjected to bisulfite treatment and then assayed for mVIM. Two assays targeting CRC-specific methylated VIM29R and one assay targeting a non-CRC-specific methylated site VIM29F with similar assay sensitivities (12.5 copies per reaction) were performed. For the VIM29R, one was the one-step PCR using the P primer set targeting a template size of 63 bp and the other was the two-step nested PCR targeting a template size of 39 by (Table 1, below).

TABLE 1

Detection of hypermethylated vimentin DNA in urine from patients with CRC.

| | Methods | | No Known Neoplasia Control (#positive/#total) | Colorectal Cancer (#positive/#total) |
|---|---|---|---|---|
| Targeted Region-VIM29R | One step MSP (P primer set) (targeting 63 bp template) | Exp. 1 | 0/10 | 0/10 |
| | Two-step MSP (targeting 39 bp template) | Exp. 1 | 0/10 | 5/10 |
| | | Exp. 2 | 0/10 | 5/10 |
| Targeted Region-VIM29F | Two-step MSP (targeting 40 bp template) | Exp. 1 | 10/10 | 10/10 |

The low MW urine DNA from both control and CRC samples were all positive for VIM29F methylation. Thus, there was at least 12.5 copies of bisulfite converted urine DNA in each sample. In two independent experiments, mVIM was detected in 50% of the CRC urine samples using a two-step nested MSP targeting VIM29R, although the methylation status of the matched CRC tissues were not determined (samples not available). None of urine samples from no known neoplasia controls were positive for VIM29R, indicating that the two-step nested MSP was sensitive and specific for the detection of mVIM in low MW DNA from 2 ml urine. However, the one-step MSP did not detect any positives from CRC and control urine samples. This indicates that the 63 bp target template in the one-step MSP assay is not sensitive enough to detect mVIM in low MW urine DNA. Collectively, this data demonstrates that two-step nested MSP assays are suitable to detect methylated CpG sites in low MW urine DNA, and the one-step MSP(P) for VIM29R was problematic because the targeted template size was too large.

14. Increase in Assay Sensitivity by Incorporating LNA into Oligonucleotide Primers The mVIM marker has been shown to exist in approximate 70-80% of CRC tissue. Our two-step VIM29R assay with a sensitivity of 12.5 copies per reaction detected 50% of mVIM in urine of CRC patients.

Figure 6:
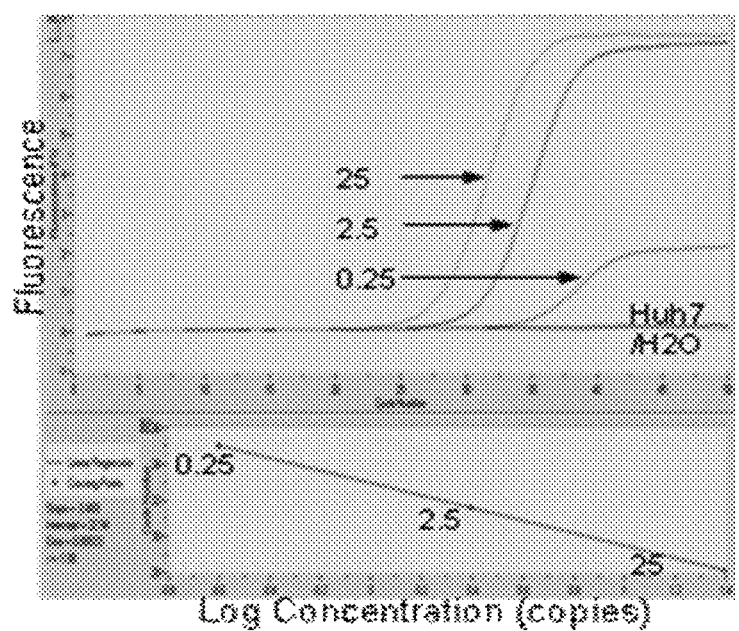
FIG. 6 depicts an amplification and standard curve demonstrating the improved sensitivity of the two-step nested VIM29R using one LNA-containing (reverse) primer and one regular primer.

The detection of mVIM in CRC urine was improved by increasing assay sensitivity using locked nucleic acid (LNA) molecules. LNA nucleotides were incorporated into the first PCR primers at the CpG sites. Various primer sets with either one LNA containing oligonucleotide or two LNA containing oligonucleotides were tested using bisulfite converted positive control and negative control DNA (data not shown). The best primer set was one with a non-LNA standard forward primer and one LNA oligonucleotide-containing reverse primer. The sensitivity of the two-step MSP using this LNA containing first PCR primer set was determined and is shown in FIG. 6. The assay with one LNA oligonucleotide primer in the first PCR can detect 1 copy of mVIM per reaction, and exhibits 10 times higher sensitivity than the assay using standard oligonucleotides as primers (data shown in FIG. 4C). Thus, the primer set containing one LNA oligonucleotide was used for subsequent studies.

15. Detection of Hypermethylated Vimentin in Colorectal Tumor and Matched Urine

After the sensitivity of VIM29R detection was improved to 1 copy per assay by incorporating LNA into the primer, a blinded study to test VIM29R was performed using matching tissue and urine DNA samples from CRC patients. DNA isolated from 20 CRC tissue and 20 urine samples of CRC patients was provided by others for this study. Low MW and high MW (>1 kb) urine DNA was obtained as described in Examples 2 and 3 above. Tissue DNA, low MW urine DNA, and high MW urine DNA were subjected to bisulfite conversion, as described in Methodology item 4, above. Bisulfite converted DNA was used in a VIM29R PCR assay using the LNA containing primer set, as described in Methodology item 14. To assess the variability of the two-step PCR assay in clinical urine samples, each low MW urine DNA sample was tested in three independent experiments. The mean and standard error of the mean of mVIM were calculated for each sample and listed in Table 2, below. The percentage of the standard error for most of triplicate data sets except two (U2 and U8) was less than 10%, showing high reproducibility. Two of the 20 high MW urine DNA samples contained detectable mVIM (data not shown).

TABLE 2

Detection of mVIM in low MW urine DNA isolated from the urine of CRC patients by the VIM29R_LNA assay

| Sample ID | Methylated VIM29R from 1 mL urine (copies) | | | | Actin* (Copies) | mVIM/actin |
|---|---|---|---|---|---|---|
| | Exp #1 | Exp #2 | Exp #3 | Mean ± SEM | | |
| U1 | 9.40 | 8.75 | 6.80 | 8.32 ± 0.78 | 400.905 | 0.02 |
| U2 | 69.79 | 193.10 | 44.12 | 102.34 ± 45.98 | 224.19 | 0.46 |
| U3 | 0.77 | 0.56 | 0.92 | 0.75 ± 0.10 | 261.675 | 0.003 |
| U4 | 5.59 | 5.90 | 5.88 | 5.79 ± 0.10 | 384.39 | 0.015 |
| U5 | 1.30 | 1.54 | 1.27 | 1.37 ± 0.08 | 1010.7 | 0.0014 |
| U6 | 2.74 | 1.85 | 2.49 | 2.36 ± 0.26 | 89.505 | 0.026 |
| U7 | ND | ND | ND | NA | 358.875 | NA |
| U8 | 58.20 | 90.00 | 83.83 | 77.34 ± 9.74 | 942.3 | 0.082 |
| U9 | ND | ND | ND | NA | 716.85 | NA |
| U10 | 80.09 | 81.23 | 78.89 | 80.07 ± 0.68 | 118.71 | 0.67 |
| U11 | 0.74 | ND | 0.55 | 0.65 ± 0.10 | 77.625 | 0.008 |
| U12 | 18.72 | 18.34 | 16.58 | 17.88 ± 0.66 | 333.36 | 0.054 |
| U13 | ND | ND | ND | NA | 86.13 | NA |
| U14 | 0.53 | 0.34 | ND | 0.44 ± 0.09 | 145.89 | 0.003 |
| U15 | ND | ND | ND | NA | 102.96 | NA |
| U16 | 0.89 | 1.2 | 0.78 | 0.99 ± 0.17 | 396.63 | 0.002 |
| U17 | ND | ND | ND | NA | 260.505 | NA |
| U18 | 11.64 | 14.86 | 12.10 | 12.87 ± 1.01 | 24.6015 | 0.52 |
| U19 | 9.28 | 8.04 | 8.28 | 8.56 ± 0.38 | 203.715 | 0.042 |
| U20 | 0.82 | 0.95 | 0.84 | 0.87 ± 0.04 | 1390.05 | 0.001 |

ND: not detectable;
NA: not applicable
*The amount of actin copy was normalized by multiplying the actin copy by 1.5% of mVIM was determined as [the amount of mVIM (mean)/Actin*] × 100%

16. Determination of the Concordance of mVIM Between Urine and Matched Tissue in a Blinded Study After the assessment of assay variability, the VIM29R assay was used to determine the amount of mVIM in the DNA isolated from CRC tissue. The results are shown in Table 3, below. mVIM was detectable in 85% (17/20) of the CRC tissue DNA samples and in 75% (15/20) of the CRC urine DNA samples. After all the samples were tested, the urine and tissue ID numbers were unblinded and matched as listed in Table 3. The concordance value between CRC tissue and matched urine was then calculated. There was a 70% concordance between the mVIM positive tissue and matched urine DNA samples. The result shows that epigenetic markers can be used in a urine test for the early detection of non-urinary cancers such as colon cancer.

TABLE 3

Detection of mVIM in tissue and corresponding urine DNA

| Pts | Matched samples IDs, after unblinding | Methylated VIM29R (copies) | | Concordance Tissue; Urine Incidence (percent) |
|---|---|---|---|---|
| | | Tissue | Urine (Mean, n = 3) | |
| A | T15/U20 | 0.18 | 0.87 | "+"; "+" |
| B | T13/U19 | 0.36 | 8.56 | 60%(12/20) |
| C | T14/U12 | 0.4 | 17.88 | |
| D | T17/U11 | 0.42 | 0.65 | |
| E | T5/U1 | 1 | 8.32 | |
| F | T12/U5 | 6.7 | 1.37 | |
| G | T18/U18 | 29 | 12.87 | |
| H | T8/U3 | 47 | 0.7 | |
| I | T20/U14 | 86 | 0.44 | |
| J | T10/U16 | 198 | 0.99 | |
| K | T9/U8 | 395 | 77.340 | |
| L | T2/U10 | 630 | 80.07 | |
| M | T16/U9 | 3.8 | ND | "+"; "−" |
| N | T4/U15 | 4.9 | ND | 25%(5/20) |
| O | T6/U17 | 12 | ND | |
| P | T19/U13 | 92 | ND | |
| Q | T11/U7 | 861 | ND | |
| R | T3/U4 | ND | 5.790 | "−"; "+" |
| S | T7/U6 | ND | 2.360 | 15%(3/20) |
| T | T1/U2 | ND | 102.34 | |
| Incidence | | 17/20 | 15/20 | |
| Percent | | 85% | 75% | |
| Concordance* | | | | 70% (12/17) |

ND: not detectable;
Concordance = # of tissue positive matched urine positive/# tissue positive × 100%

17. Human Biosample Sourcing Repository

The Great Lakes-New England (GLNE) Clinical Epidemiology and Validation Center has established a standard operating procedure for urine collection for DNA biomarker studies and has assembled a repository of samples from patients with CRC and adenoma and from clinical controls.

Sample Management Infrastructure Supported by the EDRN

Samples are collected in prelabeled and bar-coded vials and are traced by a relational database managed by a Web-fronted remote entry system. The samples and the database are also marked with HIPAA-compliant demographic and clinical data on each subject based on the EDRN Common Data Elements rules. The CLASS repository at the University of Michigan can generate bar codes to de-identify samples for blinded studies, and its database system serves as an internal control so that the location of any sample can be immediately determined.

Urine samples are collected in a standard preservative and immediately chilled by the participant. The urine samples are sent via overnight express courier to the Central Laboratory at the University of Michigan. The urine is aliquoted in 5-mL tubes and frozen at −80° C. Samples from the repository are removed and shipped overnight on dry ice. All samples are aliquoted to remove the potential bias of multiple freeze-thaw cycles.

Diagnostic Groups

Assays herein are designed to identify and/or employ biomarkers that are linked to colorectal neoplasia or early-stage colorectal adenocarcinoma for the detection of adenomas and early stages (I and II). Most colon cancers in North America and other Western countries are believed to arise from polypoid adenomas, and the progression from adenoma to carcinoma in cancer development reinforces the concept that cancers that arise from polypoid neoplasms are visible and are thus easily removed.

In contrast, hyperplastic polyps do not progress to CRC and do not exhibit the same related CRC-related biomarkers that have been found in adenoma. However, individuals with inflammatory bowel disease (IBD) and especially ulcerative colitis are at high risk for CRC, indicating that biomarkers for inflammatory and neoplastic processes may overlap. In order to retain specificity, biomarkers that occur in both processes are excluded and only those specific for neoplasia are retained. For this reason, patients with chronic bowel inflammatory processes are included as a group of biosamples that are evaluated during the clinical process of each biomarker. Finally, the control group is split into participants who have undergone a colonoscopy for screening purposes and those who have undergone a diagnostic colonoscopy because of gastrointestinal bleeding, the resection of an adenoma, or for other reasons. In summary, five diagnostic groups can be described: (1) CRC (stages I and II), (2) adenoma, (3) IBD, (4) normal colonoscopy without a diagnostic intention, and (5) normal colonoscopy with a diagnostic intention. In one determination of a panel of biomarkers, samples are obtained wherein all participants have undergone a complete colonoscopy. In one determination of a panel of biomarkers, for each diagnostic group, there are 50 subjects for a preliminary set and 95 subjects for the blinded test set. In one determination of a panel of biomarkers, samples are obtained wherein all participants have undergone a complete colonoscopy and there are 50 subjects for a preliminary test set and 95 subjects for the blinded test set.

Sources of Study Participants

A number of patient sources are used for study recruitment, which are briefly summarized here and in the tables below. All of the subjects are recruited from within the Division of Gastroenterology clinical services, and their colonoscopic procedures and detected adenomas are shown below. In addition, information is posted on Engage, a resource at the University of Michigan that currently contains information on 393 active clinical studies and averages more than 10,000 visitors per month.

The preliminary test set uses urine with matched tissue samples from approximately 50 subjects with CRC, adenoma, IBD, normal colonoscopic examination without a diagnostic intention, and normal colonoscopic examination with a diagnostic intention. The University of Michigan staff collects and supplies urine and tissue biosamples from patients from each of these categories. In addition, samples from the EDRN repository are used.

TABLE 4

Total number of sample aliquots in the CLASS repository for CRC-associated EDRN research

| Diagnosis | # Subjects | Serum | Plasma | Urine | DNA | Frozen tissue | FOBT | Stool samples | Total |
|---|---|---|---|---|---|---|---|---|---|
| CRC | 373 | 4946 | 4117 | 2395 | 356 | 1148 | 105 | 233 | 13,883 |
| Adenoma | 385 | 6158 | 5584 | 2645 | 388 | 1635 | 132 | 416 | 17,607 |
| Inflammatory bowel disease | 58 | 630 | 477 | 382 | 57 | 0 | 0 | 0 | 1604 |
| Normal + colonoscopy | 517 | 6410 | 5337 | 4122 | 457 | 61 | 79 | 311 | 17,452 |
| Normal* | 183 | 2317 | 1160 | 961 | 72 | 0 | 0 | 0 | 4693 |
| Total | 1516 | 20,461 | 16,675 | 10,505 | 1330 | 2844 | 316 | 960 | 55,239 |

*These subjects were thought to be cancer-free but did not undergo colonoscopy at the time of collection.

Case Load at the University of Michigan Medical Center

TABLE 5

Yearly subject enrollment for biomarker-based, CRC-associated EDRN research

| Diagnosis | 2004 | 2005 | 2006 | 2007 |
|---|---|---|---|---|
| Colorectal carcinoma | 92 | 11 | 38 | 80 |
| Cancer follow-up | 10 | 7 | 8 | 5 |
| Colorectal adenoma* | 14 | 13 | 93 | 62 |
| Adenoma follow-up* | 7 | 2 | 19 | 12 |
| Normal + colonoscopy | 97 | 153 | 160 | 35 |
| I Inflammatory bowel disease | 4 | 2 | 23 | 0 |
| Total | 224 | 188 | 341 | 194 |

TABLE 6

Cases of colorectal carcinoma at the University of Michigan

| Stage (AJCC) | Colorectal carcinoma | | | | Rectal adenocarcinoma | | | |
|---|---|---|---|---|---|---|---|---|
| | 2004 | 2005 | 2006 | 2007 | 2004 | 2005 | 2006 | 2007 |
| I | 25 | 19 | 35 | 16 | 7 | 6 | 13 | 5 |
| II | 28 | 28 | 19 | 17 | 8 | 9 | 8 | 11 |
| III | 39 | 26 | 28 | 23 | 13 | 13 | 10 | 8 |
| IV | 31 | 28 | 24 | 22 | 8 | 7 | 5 | 6 |
| Unknown | 8 | 6 | 9 | 9 | 7 | 3 | 5 | 4 |
| Total | 131 | 107 | 115 | 87 | 43 | 38 | 41 | 43 |

Source:
University of Michigan Medical Center tumor registry data

TABLE 7

Cases of colorectal adenomas and colonoscopies performed at the University of Michigan

| Colorectal adenoma[1] | | | | Colonoscopies performed[2] | | | |
|---|---|---|---|---|---|---|---|
| 2004 | 2005 | 2006 | 2007 | 2004 | 2005 | 2006 | 2007 |
| 821 | 855 | 870 | 845 | 9,875 | 10,010 | 9,997 | 9,963 |

Sources:
[1]Department of Pathology diagnostic data via Snomed codes.
[2]Medical Procedures Unit, GI Division, University of Michigan Hospital.

TABLE 8

Total number of sample aliquots in the CLASS repository for CRC-associated EDRN Research

| Diagnosis | # Subjects | Serum | Plasma | Urine | Frozen Tissue |
|---|---|---|---|---|---|
| CRC | 373 | 4946 | 4117 | 2395 | 1148 |
| Adenoma | 385 | 6158 | 5584 | 2645 | 1635 |
| Inflammatory bowel disease | 58 | 630 | 477 | 382 | 0 |
| Normal + colonoscopy | 517 | 6410 | 5337 | 4122 | 61 |
| Normal* | 183 | 2317 | 1160 | 961 | 0 |
| Total | 1516 | 20,461 | 16,675 | 10,505 | 2844 |

*These subjects were thought to be cancer-free but did not undergo colonoscopy at the time of collection.

18. Identification of Genetic and Epigenetic Biomarkers for Detecting Non-urinary Tract Cancer Using Low MW Urine Samples from the Human Sources Identified Above Because urine is a body fluid that includes genetic material from throughout the body, an organ-specific marker and/or a panel of molecular markers that are specific to or can identify a particular organ can be used to make a urine screening test organ specific.

Without being bound by any particular theory, because non-urinary tract cancers are genetically heterogeneous, a panel of markers is likely needed, as any single marker is unlikely to have sufficient detection sensitivity and/or specificity. Furthermore, correlated biomarkers, that is, biomarkers that correspond to expressed gene products that control gene expression such that they belong to one signaling pathway, may not provide a substantial increase in the predictive value of a biomarker panel. Accordingly, without wishing to be bound by any particular theory, a large number of correlated biomarkers are likely substantially less informative than a small number of uncorrelated biomarkers.

Here, in one example, any combination of two or more of DNA biomarkers RASSF1A (Genbank Access. # AF061836); GSTP1 (Genbank Access. # U21689); SPINT2 (Genbank Access. # U78095); CCND2 (Genbank Access. # X68452); TFPI-2 (Genbank Access. # AY044097.1); MGMT (Genbank Access. # NC_000010.10); hMLh1 (Genbank Access. # AY217549); BRAF (Genbank Access. # NC_000007.13); and BAT-26 (Genbank Access. # BD271286.1) are selected as a panel for detecting adenoma and/or colorectal cancer using low MW urine DNA. In another example, any combination of two or more of the biomarkers listed in Table 9, below, and/or any of the biomarkers listed above, are selected; the independent pathways and incidences for each are also shown.

TABLE 9

Urinary DNA markers for adenoma and CRC

| Alterations | Genes | Pathway | Incidence reported |
|---|---|---|---|
| Aberrant methylation | Vimentin | Wnt signaling pathway | 50-80% |
| | SFRP2 | Wnt signaling pathway | 77-90% |
| | Septin 9 | Cell cycle, DNA stability | 70% |
| | ITGA4 | Cell migration | 80% |
| | P16 | Rb cell cycle | 20-30% |
| | MGMT | DNA stability | 30% |
| | TFPI-2 | Cell proliferation | 90% |
| | hMLH1 | MSI; CIMP-H, DNA repair; DNA stability | 25% |
| | APC | Cell cycle, cell proliferation, apoptosis | 25-50% |
| Genetic mutations | APC | APC/β-catenin WNT pathway; cell cycle, apoptosis | 70% |
| | SMAD4 | TGF-β pathway | 10-35% |
| | P53 | P53 pathway; cell cycle, apoptosis | 30-50% |
| | K-ras | Ras/raf pathway; cell proliferation, apoptosis | 30-50% |
| | BRAF | Ras/raf pathway; cell proliferation, apoptosis | 15-25% |
| | BAT-26 | MSI; CIMP-H, DNA stability | 40-50% |

19. Characterized Urine Samples for Biomarker Panel Selections

The frequency of detecting the genetic mutated K-ras DNA as an indication of adenoma and/or colorectal cancer in various body fluids including urine in a modified restriction endonuclease-enriched PCR (RE-PCR) test was determined, performed as described in the above Examples. The results are reproduced in Table 10. As compared to plasma or serum, using total urine resulted in a more accurate (higher) detection rate.

TABLE 10

Detection of mutated K-ras DNA in the body fluids of 20 patients with detectable K-ras mutations in their corresponding colorectal disease tissue

| | (A) 200 µL body fluid | | | (B) 10 µL body fluid | | |
|---|---|---|---|---|---|---|
| | Urine | Serum | Plasma | Urine | Serum | Plasma |
| # of samples in which mutations were detected/# of samples tested | 19/20 | 7/20 | 8/20 | 8/20 | 6/20 | 11/20 |
| Percent detection | 95% | 35% | 40% | 40% | 30% | 55% |
| P value | — | 0.00014 | 0.00043 | — | 0.741 | 0.527 |

Further, the use of low MW DNA from urine isolated by agarose gel electrophoresis, or alternatively, using carboxylated magnetic beads, resulted in a higher concordance between the K-ras mutations detected in CRC tissue (83% using low MW DNA versus 31% detection rate using total urine DNA, P<0.5 and P<0.005, respectively). The results are reproduced in Table 11.

TABLE 11

Correlation between the detection of K-ras mutations in tissue and their corresponding low MW urine DNA fraction or total urine DNA

| # of Mutated K-ras Detected $(T, U_T, U_L)^2$ | | CRC (n = 59) | Adenoma (n = 32) | Hyperplastic polyps (n = 2)* | NKn[1] (n = 77) |
|---|---|---|---|---|---|
| (+, +, +) | | 16 | 17 | 0 | # of urine |
| (+, −, +) | | 31 | 9 | 1 | samples |
| (+, −, −) | | 3 | 3 | 0 | positive for |
| (−, +, +) | | 4 | 0 | 0 | K-ras |
| (−, −, +) | | 3 | 1 | 0 | mutation = |
| (−, −, −) | | 2 | 2 | 1 | 20 (26%) |
| Concordance | Total urine DNA | 18/59 (31%) | 18/32 (56%) | 0/2 (0%) | N/A |
| | Low MW urine DNA | 49/59 (83%) | 28/32 (87.5%) | 2/2 (100%) | N/A |

[1] No known neoplasia (NKn) represents patients who were negative for neoplasia following colonoscopy in the GI clinics.
[2] The mutated K-ras DNA was detected "+" or undetected "−" when the tissue DNA (T), total urine DNA ($U_T$), or low MW urine DNA ($U_L$) from the same individual was used in the assays.
* Statistical analysis was not performed for hyperplastic polyps because of the small sample size or for the NKn group because no tissue DNA was available.

As K-ras mutations do result in false positives, and for the additional specificity reasons mentioned above, the aberrant methylation of additional biomarkers are included. Here, the hypermethylation of the ITGA4 (mITGA4) gene was evaluated for use as a biomarker. The results are shown in Table 12.

TABLE 12

Detection of promoter-hypermethylated ITGA4 in the urine of colorectal disease patients

| Urine DNA | CRC | | Adenoma | | Hyperpastic polyps | | Control | |
|---|---|---|---|---|---|---|---|---|
| | Total | Low | Total | Low | Total | Low | Total | Low |
| # Positive/# tested | 6/17 | 5/16 | 2/8 | 2/8 | 1/6 | 0/6 | 12/25 | 0/10 |
| Percent positive | 35.3% | 31.3% | 25% | 25% | 16.6% | 0% | 48% | 0% |

The results show that very little, if any, mITGA4 was detected in the group with hyperplastic polyps or in the control groups when low MW urine DNA was used; in contrast, 31% of CRC samples and 25% of adenomas were shown to contain detectable levels of mITGA4 for both the low and high MW urine DNA (Table 12). These data show that (1) hypermethylation of the ITGA4 gene may occur frequently in sloughed-off cells from the urinary tract but does not occur significantly in cells that contribute DNA to the circulation; (2) circulation-derived hypermethylated DNA can be detected in urine; and (3) the inclusion of mITGA4 in a urine test using low MW DNA as the substrate could reduce the false-positive rate for CRC detection.

Here, the frequency of detecting the aberrant methylation or mutations, preferentially the biomarkers in Example 18 and/or Table 9, are determined using RE-PCR, preferentially using low MW DNA isolated using carboxylated magnetic beads. Additionally, other biomarkers known in the art to correlate with adenomas and/or CRC are similarly determined. Additionally, other biomarkers known in the art to correlate with HCC or non-urinary tract associated cancers are detected.

20. Detection in Urine of Genetically or Epigenetically Modified DNA Markers for the Screening/Early Detection of Adenoma and CRC Herein, DNA biomarkers are evaluated to determine whether DNA markers known to occur in adenoma or CRC are found in the urine of patients with adenoma or CRC based on a concordance study. To this end, the PCR-based assays (for example, suitable for DNA substrates shorter than 300 bp to detect the aberrant promoter hypermethlyation of tumor suppressor genes) successfully applied for detection of CRC-related mutated K-ras gene mutations and hypermethylated vimentin and ITGA4 in urine of CRC patients, as described above, are employed.

The DNA biomarkers are categorized in two groups: (1) genetic mutations and (2) epigenetic modifications. The adenoma- or CRC-related genetic mutations include mutations in K-ras, p. 53, BRAF, and BAT-26. Epigenetic modifications, promoter hypermethylation, in VIM, ITGA4, p16, MGMT, TFPI-2, hMLH1, and APC are used as urine biomarkers for adenoma or CRC. In addition, other DNA biomarkers are employed and/or evaluated based on the state of the art. Where aberrant methylation is detected, bisulfite treatment is employed as described above, and detected by DNA sequencing, regular PCR using methylation specific PCR, as described in Baylin S B, Herman J G, Graff J R, Vertino P M, Issa J P, "Alterations in DNA methylation: A fundamental aspect of neoplasia," Adv Canc Res., 1998, 72: 141-96, herein incorporated by reference in its entirety, or real time PCR (also called MethyLight), using an additional methylation-specific TaqMan probe as described in Eads C A, Danenberg K D, Kawakami K, Saltz L B, Blake C, Shibata D et al., "MethyLight: a high-throughput assay to measure DNA methylation," Nucl Acids Res 2000, 28:e32 i-e32 vi., herein incorporated by reference in its entirety.

If one assay detects 50% or more of urine samples containing the methylated marker from marker-positive patients, then by extension, three assays targeting three nonoverlapping disease-related CpG clusters, if available, detects 100% of urine samples from marker-positive patients. Thus, herein biomarkers are preferentially selected for use with other biomarkers. In the experiments described above with mVIM, although the mVIM status of disease tissue is unavailable, 50% of urine samples from CRC patients were found to be positive to mVIM with the VIM29R two-step PCR assay.

To enhance the sensitivity of a urine test to detect adenoma- and CRC-specific aberrant hypermethylation, up to 3 MS-PCR assays are designed using appropriate primers to target different adenoma or CRC-specific CpG clusters for each candidate gene.

The biomarkers are evaluated based on sensitivity and specificity. For example, the aberrant methylation of the vimentin gene (mVIM) is detected as shown above, and also as shown in other studies to have the highest sensitivity and specificity of any CRC-related hypermethylation marker. Further, a two-step nested MethyLight PCR is optionally used to determine methylated markers that are in turn used in combination with an analysis of mVIM, IGTA4, or both to detect adenoma and/or colon cancer.

To perform the two-step nested MethyLight assays, the target CpG sites are identified and the primer sequences for PCR are designed, PCR conditions are optimized, and the specificity of the assay to CRC is tested using appropriate positive and negative control DNA from different cell lines.

To determine the sensitivity of each assay, samples are prepared by spiking 1, 10, 100, and 1000 of copies of positive control DNA isolated from a CRC cell line (e.g., WiDr for mVIM) into 50 ng/μL of negative control DNA (HepG2 DNA for mVIM). After the assay is performed, its range of linearity and its coefficient of variation at 10 methylated copies per 50 ng DNA are assessed. Preferentially, an assay sensitivity of approximately 10 copies in about 50 ng of unmethylated genomes per assay is used to identify biomarkers.

Fifty nanograms of negative control DNA is used to determine assay sensitivity because more than 95% of urine specimens contain less than 250 ng DNA per mL based on a previous analysis of more than 200 urine specimens, and the DNA isolated from approximately 200 uL of urine is used in each assay.

Assays not achieving an initial sensitivity of 10 copies/50 ng of unmethylated genomic DNA, are optimized, such as by optimizing the PCR conditions by changing the $Mg^{2+}$ concentration, the annealing temperature, the manufacturer of the Taq polymerase, or the use of an unmethylated, sequence-specific locked nucleic acid (LNA) to inhibit amplification of unmethylated sequences, but not of the target sequence. When necessary, primers are redesigned to enhance the amplification efficiency.

After the sensitivity of an assay is established to be 10 copies/50 ng of unmethylated DNA, the concordance value between urine and its matched tissue for each marker is determined. In addition, quantitative LNA-clamping, PCR-based assays for the genetic mutations in Table 9 above are developed using the methods used to detect the K-ras codon in urine described in the above examples.

In one assay, the genetic mutations in p53, APC, BRFA, and BAT-26 are evaluated. The assays detecting point mutations in p53 (8 codons: 175p. 2, 245p. 1, 245p. 2, 248p. 1, 248p. 2, 273p. 1, 273p. 2, 282p. 1) and APC are different than those for the K-ras, BRAF, and BAT-26 mutations. In order to reduce the amplicon size while detecting p53 mutations, a Simple Probe (Roche) or a Minor Groove Binding (MGB) probe is optionally used instead of a hybridization probe. (A TaqMan probe is not used when it is necessary to perform melting curve analysis at the end of a PCR reaction.)

Not wishing to be bound by any particular theory, LNA oligomers improve allele-specific PCR by suppressing the amplification of the background variant; the amplification of wild-type templates is inhibited by the stable binding of a wild-type-specific LNA to wild-type templates, whereas the binding of the LNA to mutated templates is not stable during amplification due to a 1-bp mismatch, which permits amplification to proceed with the mutated templates. After amplification, the amplified products are analyzed by melting curve analysis.

As an example, four different species of LNA molecules and two sets of primers are designed for two different PCR reactions to detect the p53 point mutations, respectively. One LNA covers the sequence of codon 175; the second covers codons 245 to 249; the third covers codon 273; and the last one covers codon 282. One set of primers amplifies the region that includes codon 175 with LNA molecules covering codon 175. Another set of primers applifies the region covering codons 245 to 282 in the presence of one of three other species of LNA molecules. At the end of PCR, the specific mutation in the p53 gene is identified using melting curve analysis with DNA standards of known sequences.

The sensitivity of each assay for the detection of mutated sequences is determined using a reconstituted, that is, a standard spiked with positive control DNA. The positive control is DNA from a cell line known to contain the specific mutations or DNA that is constructed by cloning the mutated sequence into a plasmid vector. HepG2 DNA is used as wild-type control DNA, because none of the DNA modifications of interest occur in this cell line. Assay calibration is assessed by observing the quantitative LNA-clamping, PCR-based assay in 50-ng/μL samples of HepG2 DNA spiked with 1 to 1000 copies of mutated DNA. The range of linearity of the assay is confirmed and the coefficient of variation at 10 mutated copies per 50 ng DNA is calculated.

Using the highly sensitive assays described above in this Example, the last step in establishing a DNA biomarker is determining the concordance between urine and matched tissue samples for each DNA marker using the human biosamples described above. Detected sequences with good concordance are selected as biomarkers. For example, material from 25 patients with adenoma and 25 patients with CRC are used, for a total of 50 pairs of matched urine and tissue clinical samples. DNA is isolated from the urine and tissue sections, and the assays developed in this Example are used to detect the DNA markers of interest. To construct the calibration curves, every assay is performed with a reconstituted (spiked) standard.

Not wishing to be bound by any theory, because the samples consists of matched urine and tissue samples from 25 patients with adenoma and 25 with CRC, a range of values for both the tissue and urine samples is produced. For each marker, scatterplots to determine linearity and 95% confidence intervals are determined for the tissue and urine samples. If the relationship is not linear, the assays are transformed, or a nonlinear analysis is developed. For each marker, the null hypothesis ($H_o$: $\rho<0.5$) is tested ($\alpha=0.05$), and a rejection of the null hypothesis demonstrates that the marker is sufficiently correlated between the tissue and urine samples and is thus a worthwhile candidate for the urine panel. If the correlation between urine and tissue in the population, $\rho$, is at least 0.75, the power to reject the null hypothesis is at least 90%.

Furthermore, selecting biomarkers is optionally performed in a sequential manner based on the frequency of incidence. Preferentially, positivity (i.e., an incidence of cancer) is defined at the level of the gene but not at the level of a specific codon or CpG site/cluster. Thus, assay showing a positive value (above the cutoff point) for DNA isolated from tissue or urine, is scored as "positive" for this particular gene as "mutated/modified" regardless of the specific codon or CpG site/cluster of the modification. For example, DNA samples shown to contain a mutation in codon 175 of the p53 gene do not require testing for the p53 codon 249 mutation, but may be optionally tested. Furthermore, mutations found in the tissue sample but not in the urine sample, can be optionally selected as a biomarker, further optimized, and reevaluated for use with urine samples.

Optionally, biomarkers are selected based on a value of concordance of 75% or greater between urine and tumor samples with sensitivities and specificities that match or exceed those found in tumors. In addition, further selection is based on the prevalence of the markers and/or their ability to distinguish adenoma or CRC samples from subjects with no known neoplasia.

21. Clinical Characterization of Urinary DNA Biomarkers for the Early Detection of CRC Preferentially, biomarkers have a collective sensitivity and specificity that is high enough to identify individuals who do not require colonoscopic screening because of their relatively low neoplastic risk at the time of screening. This characterization is accomplished using unsupervised and supervised learning methods for analyzing the data sets to determine whether patients with CRC and adenomas are distinguished from healthy individuals using a certain panel of biomarkers.

Thus, verification of the reproducibility of the analytical method and the sampling within and between days for the same urine analyte is performed. Verification can critical for planning a large cross-sectional validation study of these assays. Two feasibility issues are considered in the design. First, when using EDRN samples, the samples are used for multiple validation studies, and therefore multiple types of biosamples from each participant are obtained. Second, other factors such as fasting, nonfasting, and diurnal variations that would be encountered in clinical practice are considered when collecting specimens. Many, if not all, specimens collected to date in the EDRN and University of Michigan repositories have been from fasting subjects.

For analytical validation, urine samples with matching paraffin-fixed tissue samples from 30 patients with CRC and 30 healthy normal participants are used. Each participant is sampled over no more than 2 weeks. The urine samples are morning samples taken after 8 to 12 hours of fasting, nonfasting in the morning, and nonfasting in the afternoon. A total of 240 samples are run in duplicate. The participants are the same as those studied above and are sampled once; whether the patient was fasting or not is noted, along with the time the sample was taken.

The SAS POWER procedure (Two Sample t Test for Mean Difference) is used to calculate power estimates. The sample size is 30 in each of the CRC and control group. Quantitative biomarkers are measured in urine samples collected at three time-points and also in matched paraffin-embedded tissue sample (to be measured only once) for each subject. Each measurement is assumed to approximate normal distribution after standardization to mean of zero ($\mu=0$) and standard deviation of one (SD=1). Here, two-sided type 1 error rate ($\alpha$) is assumed 0.01 under overall $\alpha=0.05$ after correction for multiple tests in examining mean differences between CRC and control groups with consideration of fasting status and diurnal variations within and across subjects. With assumption of equal variances, the verification assays using a sample size of 30 have at least 80% and 99% power in detecting mean differences of at least 0.9 SD and 1.1 SD, respectively. Further, it is determined whether sex is a confounding factor for the above-mentioned association tests; sex-specific association tests are performed if in actual data analysis where sex is a significant predictor of CRC status. While all the assumptions hold true and 50% females (and 50% males) in the overall data, using 15 sex-specific CRC subjects and 15 sex-specific controls, has $\geq 80\%$ and $\geq 99\%$ power in detecting mean differences of at least $\geq 1.3$ SD and $\geq 1.9$ SD, respectively. Together, the assays exhibit sufficient detection power for mean differences of identified biomarkers between CRC cases and controls and between other necessary comparison groups.

Herein, the reproducibility of detecting urinary molecules in different samples is determined, such as samples taken at different times of the day from the same patient. The individualized panel of molecular signatures of each patient is used to determine the reproducibility of both the quantity and quality of each signature from varied urine samples collected from each individual. In one example, the two most qualified DNA markers (high sensitivity and specificity) from the panel of urinary biomarkers are used to analyze sampling reproducibility. A sample size of 15 men and 15 women in each category are selected to prevent gender bias.

Descriptive statistics (e.g., mean, median, standard deviation, confidence intervals) and graphical displays (e.g., box plot, scatterplot, and histogram) are used to characterize the between-strata and within-stratum distributions of the assay results including the influence of gender. Maximum likelihood estimates of between-subject, between-day, and within-day variance components are calculated using linear mixed models. The similarity of fasting versus nonfasting and nonfasting morning samples versus afternoon samples from healthy normal subjects and those from patients with CRC is determined. When fasting or time of day significantly alters the classification of participants, future samples are drawn in the prescribed manner (i.e., fasting).

Preliminary Clinical Characterization: Preliminary Testing Set

Preliminary decision analysis data (sensitivity, specificity, receiver operating characteristics [ROC] curves) is generated from an open-label, unblinded preliminary testing set, which provides information on variance that is used to modify the design of subsequent validation steps when necessary. In one preliminary testing set, urine samples from 50 healthy normal participants who had a colonoscopy performed without a diagnostic intention, 50 healthy normal participants who had a colonoscopy performed with a diagnostic intention, 50 participants with IBD, 50 participants with adenomatous polyps of 1 cm or greater, and 50 participants with stage I/II CRC are used from the EDRN repository, for a total of 250 participants, which is an adequate number based on power analysis, as described below. Each participant is sampled once. Each urine sample is assayed once for DNA markers as described above.

SAS POWER procedure (Fisher's Exact Conditional Test for Two Proportions) is used to estimate power. Sample size is 50 subjects for each of five groups from healthy normal to CRC. As multiple tests are involved, a two-sided type 1 error rate $\alpha$ of 0.01 (overall $\alpha$ of 0.05) is assumed here for power calculation. If 70% (or 35 of 50) subjects tested and defined as positive for a designated quantitative biomarker is assumed, then the preliminary testing set has at least 80% power to detect at least 35% group proportion difference, that is, no more than 35% (17 to 18 of 50) subjects tested and defined as positive for a designated quantitative biomarker in group 2 (in this case, sensitivity of 70%, and specificity of 65% or better). Power would reach 99% when proportion difference reaches at least 50%, that is, no more than 20% (10 of 50) subjects tested and defined as positive for a designated quantitative biomarker in group 2 (in this case, sensitivity of 70%, and specificity of 80% or better). In general, the preliminary testing set has sufficient power to discriminate proportion difference of 35% or greater with sensitivity and specificity of 70% or better. Power would further enhance along with an increased sensitivity and/or specificity (consequently increased areas under the receiver operating characteristic curves) for a successfully identified biomarker or a successfully identified combination of multiple biomarkers in this proposal.

To identify markers for clinical diagnosis, to define cutoff points to eliminate false positives, and to obtain better specificities, the sensitivity and specificity values from a large set of samples is calculated. Logistic regression is used to construct multimarker prediction rules with cross-validation used to construct unbiased estimates of sensitivity and specificity. Based on these estimates, cutoff points for multimarker models are fixed for blinded test sets.

Not wishing to be bound by any particular theory, PCR produces some false positives, which are either pathological false positives or assay (or biochemical) false positives. Although assay false positives are overcome by further optimization and characterization as performed as described herein, pathological false positives, which indicate that the marker is in urine but is not relevant to the diagnosis of adenoma or CRC, optionally appear in some instances because urine contains DNA derived from the entire body. To prevent the impact of pathological false positives, cutoff points or a multimarker model are determined.

Cutoff points are optionally defined to prevent pathological false positives if the high assay sensitivity leads to the detection of the marker of interest in a significant portion of the urine samples from patients with healthy, normal colons. Cutoffs can be especially important because a significant portion of circulating urine DNA is derived from cells undergoing apoptosis, which is often triggered by spontaneous or basal-level modifications that may not be relevant to CRC or to other pathological conditions (e.g., different types of cancers). If, an aberrant methylation or genetic mutation is related to pathological conditions such as a tumor elsewhere in the body, defining cutoff points will not eliminate a false positive for adenoma or CRC.; accordingly, as described above, organ specific biomarkers are optionally included as controls in a diagnostic assay employing detection of the selected biomarkers. Regardless, it is important in such instances to detect the true pathological cause so that an individual is referred for other diagnostic methods such as a colonoscopy. Furthermore, the use of multiple biomarkers reduces the number of false positives for adenoma or CRC, as it does with other non-urinary tract associated cancers being detected.

The ability of the biomarkers to discriminate between patients with stage I/II cancer and those who are healthy normal controls or who have adenomas is also assessed using the preliminary testing set. The effect of gender on the ROC for each setting is also examined. With regard to statistical analysis, the primary analysis is multiple logistic regression with receiver operating characteristic curves (SAS LOGISTIC procedure). Many simulation reports express the usefulness of predictive variable testing as the areas under the receiver operating characteristic curves, which reflect the combination of sensitivity and specificity parameters. In general, an area under the curve of 0.5 is non-discriminatory. It is widely accepted that an area under the curve can be used for screening if it is >0.8, and it can be used for pre-symptomatic diagnosis if it is >0.99. Here, discrete CRC status is the response variable, and quantitative biomarker is a predictive variable, together with some potential covariates (such as age, sex, etc). Parameters including sensitivity, specificity, false positive value, and positive predictive value are derived from the receiver operating characteristic curves output. Alternatively, or in addition, stepwise, canonical and discriminant function analyses (SAS DISCRIM or CANDISC procedure) are considered to render convenience in sorting out meaningful predictor variables using multiple attributes. Penalized discriminant analysis is optionally used in assessing highly-correlated predictive variables, for example for some related biomarkers sharing the same or similar known biological pathways. Other newly developed Bayesian and/or random forests methods are optionally integrated to the data assessment, especially for detection of pre-clinically meaningful joint and/or interacting effects of multiple predictive or diagnostic clinical biomarkers.

Blinded Test Set to Select Biomarker(s) for a Large-scale Study and for High-throughput Assay Development.

Preliminary decision analysis data (sensitivity, specificity, ROC analysis) is also generated from a blinded test set to produce both sufficient evidence of discrimination and sufficient information to design a large validation study. To avoid overfitting, the test set consists of samples obtained from different patients than those assayed above in the preliminary testing set. These samples provide preliminary biomarker decision analysis data.

Urine samples are obtained from 95 healthy normal individuals who had a colonoscopy without a diagnostic intention, 95 healthy normal participants who had a colonoscopy with a diagnostic intention, 95 patients with IBD, 95 participants with adenoma, and 95 patients with stage I/II CRC. The 475 participants are sampled once, and each urine sample is assayed once. The assays are performed with blinding as to the disease status.

Similarly, SAS POWER procedure (Fisher's Exact Conditional Test for Two Proportions) is used to estimate power. Sample size here is 95 subjects for each of five groups. Since multiple tests are involved, two-sided $\alpha$ of 0.01 (overall $\alpha$ of 0.05) is assumed for power calculation. If 70% (or 66 of 95) subjects tested and defined as positive for a designated quantitative biomarker is assumed, then the blinded testing has at least 80% power to detect at least 25% group proportion difference, that is, no more than 45% (43 of 95) subjects tested and defined as positive for a designated quantitative biomarker in group 2 (in this case, sensitivity of 70%, and specificity of 55% or better). Power would reach 99% when proportion difference reaches at least 35%, that is, no more than 25% (24 of 95) subjects tested and defined as positive for a designated quantitative biomarker in group 2 (in this case, sensitivity of 70%, and specificity of 75% or better). Taken together, the blinded testing has sufficient power to discriminate proportion difference is 25% or greater with sensitivity and specificity of 70% or better. Actual power further improves for a successfully identified biomarker or a combination of biomarkers that exhibit sufficient sensitivity and/or specificity.

Sensitivity and specificity values and 95% confidence intervals are calculated for each model based on the rules generated from the open-label data in the preliminary testing set. Markers and combinations of markers in adenoma or CRC samples are compared with markers in IBD and no known neoplasia using multiple logistic regression analysis. Logistic regression models using the branch and bound algorithm for best-subsets selection is used to determine which individual markers and which combinations of markers are the best predictors of disease status. Subgroup analyses is optionally performed to determine whether the models perform differently on groups characterized by smoking status or by gender. These sample sizes allow estimation of sensitivities and specificities with standard errors of approximately 0.05 or less.

The samples are unblinded to test the null hypotheses that the sensitivity is at least 60% and specificity is at least 90% ($\alpha=0.05$). If the true sensitivity is at least 70% and the true specificity is at least 95%, the probability of rejecting the null hypotheses is at least 0.8.

The current state-of-the-art noninvasive screening method for CRC, the fecal occult blood test (FOBT), has a sensitivity of 33% and a specificity of 95, as described in 137, hereby incorporated by reference. To supplement or replace FOBT and reduce or eliminate colonoscopic screening, the sensitivity and specificity of a urine test are based in part on its screening performance as compared with the current state-of-the-art standard.

To be considered for further development, a selected biomarker preferentially meets at least one of two sets of standards: (1) The biomarker exceeds the predictive value of FOBT as a single biomarker or (2) it must has an added value to a putative panel of adenoma or CRC urine biomarkers. For example, a marker with a low sensitivity but a high specificity may not qualify as an independent marker for adenoma or CRC but could increase the predicative value in combination with other biomarkers due to its high specificity.

A marker selected because it passes either standard is optionally used in the high-throughput assays described below. The high throughput assays preferentially use markers selected by the methods of this Example.

Other Cancers

Examination of 20 urine samples each from patients with hepatocellular carcinoma (HCC) or other cancers permits the determination of whether any of the individual urine markers identified above are altered in other non-urinary tracted cancers. The HCC samples are provided by the University of Michigan, The proportions of samples in each category classified as normal or CRC/adenoma, along with 95% exact binomial confidence intervals, are calculated.

Preferentially, a panel or panels of urine markers specific for monitoring the population that is at high risk (age >50 years) is/are identified for the development of adenoma or CRC or other non-urinary tract cancers. Identifying a marker as positive for other cancers would not necessarily exclude that marker from a panel for detecting adenoma or CRC because the specificity for adenoma or CRC should increase with a combination of other markers. The usefulness of each marker is evaluated alone and in a panel. Optionally, if a marker has a correlation coefficient of at least 0.75 with any of the other cancers, then the marker is selected.

22. Development of a Multiplex PCR-based Assay

A multiplex real-time fluorescent detection assay is designed and performed in a high-throughput format that permits quantitative measurements. Several technologies for developing high-throughput multiplex real-time PCR assays have been used and are commercially available, such as the Qiagen Multiplex PCR Kit (Valencia, Calif.) and the Easy-Plex products (AusDiagnostics, Sidney, Australia). Herein, the platform for the assay is uses the same platform developed for the candidate markers. For example, the MGB Eclipse Detection System (Sigma, St. Louis, Mo.), has been shown to give a highly specific and sensitive fluorescent result (probes can detect one target copy) and uses 5'-MGB-quencher-oligonucleotide-fluorophores that fluoresce upon hybridization to the complementary target. By attaching different fluorophores to the MGB Eclipse probes, up to eight target sequences can be detected in a single reaction. Primer design software and the dye/quencher combinations are available for free from many probe providers such as Biosearch Technologies (Novato, Calif.).

To develop the multiplex PCR-based assay, DNA is isolated from the preliminary testing sample set before designing and performing high-throughput assays using the urine DNA isolated from a blinded test set as described herein. The sensitivity and selectivity of each multiplex real time fluorescent assay is determined and compared to the assays described above.

23. Development of the Padlock Probe-mediated DNA Microarray

Padlock probe-mediated amplification has been used to detect mutations, single-nucleotide polymorphisms (SNPs) as described in, and microRNAs (~25 nt in length) as described in. Padlock probe mediated amplification exhibits great sensitivity and specificity. In the assay, probes are designed to anneal to their target sequence at the 5' and 3' ends of the padlock probe, designed in such a way as to leave a nick in the DNA. Ligation occurs specifically at the nick in the double-stranded DNA and the specificity of this padlock ligation has been demonstrated extensively to be adequate for even single nucleotide polymorphisms (SNPs).

Herein, padlock probe mediated amplification is used to detect aberrant methylation of circulation derived low MW DNA in urine samples. It is also used to detect both genetic and epigenetic, circulation derived urinary DNA markers in a high-throughput DNA microarray format.

Each padlock probe for biomarker contains three sequences: (1) the gene-specific sequence at the 5' and 3' ends of the probe, (2) the artificial forward primer sequence (F), and (3) the complementary sequence to the artificial reverse primer sequence (R). The only difference between the padlock probes is the gene-specific sequences, while the F and R sequences will remain the same.

Herein, padlock probe are designed and tested for each biomarker. Padlock probes are contacted with a low MW urine sample and/or total urine DNA and subject to ligation and PCR amplification. All of the padlock probes are combined as a cocktail for use in the multiplex PCR described above. Specifically, Tthe cocktail of padlock probes are mixed with DNA substrates, denatured, annealed to its complementary sequences, and ligated by the thermal-stable AmpLigase (Epicentre Biotechnologies). After ligation, the reaction is subject to PCR amplification with the artificial primer set, F/R where the 3' of the R primer are labeled with Cy3 for detection on a DNA microarray. The PCR products are then hybridized to a high-density microarray chip printed with gene-specific oligonucleotides and quantified, for example, by a scanner.

The above examples are illustrative only and are not meant to limit the claimed subject matter. One of skill in the art understands that the assays and selection of biomarkers performed for one particular non-urinary tract cancer can be performed to design and implement diagnostic and prognostic assays for other non-urinary tract cancers.

What is claimed:

1. A method for detecting aberrant hypermethylation of the vimentin gene comprising:

obtaining a biological sample derived from a subject; and
  subjecting said sample to a two-step nested real time PCR assay wherein the first PCR primer set of a forward primer having the sequence of gctcttcgtggtgtggtgcggt-tcgggtatcgc (SEQ ID NO:5) and a reverse primer having a sequence of gctcttcgtggtgtggtgctccGactaaaactcGacc (SEQ ID NO:6), wherein the twenty-third guanine residue and the thirty-fourth guanine residue are locked nucleic acid residues; and the second PCR primer set of a forward primer having the sequence of gtgtggtgcggtt (SEQ ID NO: 51) and a reverse primer having the sequence of gtgtggtgctccga (SEQ ID NO: 10), and a probe of FAM-atcgcgagtcggtcgagtt-BHQ 1(SEQ ID NO: 9), thereby determining the absence or presence of aberrant hypermethylation of the vimentin gene in said subject.

* * * * *

SEQUENCE LISTING

<160> NUMBER OF SEQ ID NOS: 51

<210> SEQ ID NO 1
<211> LENGTH: 19
<212> TYPE: DNA

-continued

<213> ORGANISM: Artificial Sequence
<220> FEATURE:
<223> OTHER INFORMATION: Description of Artificial Sequence: Synthetic
      primer

<400> SEQUENCE: 1
gatgtatgaa ggttttttgg                                                 19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctaactacct ccacccactc                                                 20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccgtggtcct gaaccagtta                                                 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtcgcctgtt caccaaggat                                                 20

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gctcttcgtg gtgtggtgcg gttcgggtat cgc                                  33

<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(23)
<223> OTHER INFORMATION: Locked nucleic acid
<220> FEATURE:
<221> NAME/KEY: modified_base
<222> LOCATION: (34)..(34)
<223> OTHER INFORMATION: Locked nucleic acid

<400> SEQUENCE: 6

```
gctcttcgtg gtgtggtgct ccgactaaaa ctcgacc                              37
```

<210> SEQ ID NO 7
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
gtgtggtgcg gttc                                                       14
```

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
gtgtggtgct ccgac                                                      15
```

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' BHQ1

<400> SEQUENCE: 9

```
atcgcgagtc ggtcgagtt                                                  19
```

<210> SEQ ID NO 10
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
gtgtggtgct ccga                                                       14
```

<210> SEQ ID NO 11
<211> LENGTH: 410
<212> TYPE: DNA
<213> ORGANISM: Homo sapiens

<400> SEQUENCE: 11

```
gctgggatgg cagtgggagg ggaccctctt tcctaacggg gttataaaaa cagcgccctc     60 ggcgggtcc agtcctctgc cactctcgct ccgaggtccc cgcgccagag acgcagccgc    120
gctcccacca cccacaccca ccgcgccctc gttcgcctct tctccgggag ccagtccgcg    180
ccaccgccgc cgcccaggcc atcgccaccc tccgcagcca tgtccaccag gtccgtgtcc    240
tcgtcctcct accgcaggat gttcggcggc ccgggcaccg cgagccggcc gagctccagc    300
cggagctacg tgactacgtc cacccgcacc tacagcctgg gcagcgcgct gcgccccagc    360
accagccgca gcctctacgc ctcgtccccg ggcggcgtgt atgccacgcg               410
```

<210> SEQ ID NO 12
<211> LENGTH: 404
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
gttgggatgg tagtgggagg ggattttttt ttttaacggg gttataaaaa tagcgttttc      60
ggcgggtttt agttttttgt tattttcgtt tcgaggtttt cgcgttagag acgtagtcgc     120
gtttttatta tttatattta tcgcgttttc gttcgttttt ttttcgggag ttagttcgcg     180
ttatcgtcgt cgtttaggtt atcgttattt ttcgtagtta tgtttattag gttcgtgttt     240
tcgttttttt atcgtaggat gttcggcggt tcgggtatcg cgagtcggtc gagttttagt     300
cggagttacg tgattacgtt tattcgtatt tatagtttgg gtagcgcgtt gcgttttagt     360
attagtcgta gttttacgt  ttcgttttcg ggcggcgtgt atgt                      404
```

<210> SEQ ID NO 13
<211> LENGTH: 300
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
atcgtaggat gttcggcggt tcgggtatcg cgagtcggtc gagttttagt cggagttacg      60
tgattacgtt tattcgtatt tatagtttgg gtagcgcgtt gcgttttagt attagtcgta     120 gttttacgt  ttcgttttcg ggcggcgtgt atgttacgcg ttttttttgtc gtgcgtttgc     180 ggagtagcgt gttcggggtg cggttttttgt aggattcggt ggattttttcg ttggtcgacg     240 ttattaatat cgagtttaag aatattcgta ttaacgagaa ggtggagttg taggagttga     300
```

<210> SEQ ID NO 14
<211> LENGTH: 285
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (282)..(282)
<223> OTHER INFORMATION: a, c, t or g

<400> SEQUENCE: 14

```
gttcggcggt tcgggtatcg cgagtcggtc gagttttagt cggagttacg tgattacgtt      60
tattcgtatt tatagtttgg gtagcgcgtt gcgttttagt attagtcgta gttttacgt     120 ttcgttttcg ggcggcgtgt atgttacgcg ttttttttgtc gtgcgtttgc ggagtagcgt     180
gttcggggtg cggttttttgt aggattcggt ggattttttcg ttggtcgacg ttattaatat     240
cgagtttaag aatattcgta ttaacgagaa ggtggactgg tngga                     285
```

<210> SEQ ID NO 15
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gcgttttagt attagtcgta gttttttacgt tcgttttcg ggcggcgtgt atgttacgcg    60 ttttttgtc gtgcgtttgc ggagtagcgt gttcggggtg cggtttttgt aggattcggt   120 ggattttcg ttggtcgacg ttattaatat cgagtttaag aatattcgta ttaacgagaa   180
ggtggagttg taggagttga                                               200

<210> SEQ ID NO 16
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (67)..(69)
<223> OTHER INFORMATION: a, c, t or g

<400> SEQUENCE: 16
ttcgtcatcg ggcggcgtgt atgttacgcg cttttttgtc gtgcgtttgc ggagtagcgt    60
gttcggnnng cggtttttgt aggattcggt ggattttcg ttggtcgacg ttattaatat   120
cga                                                                 123

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24
<400> SEQUENCE: 24
000

<210> SEQ ID NO 25
<400> SEQUENCE: 25
000

<210> SEQ ID NO 26
<400> SEQUENCE: 26
000

<210> SEQ ID NO 27
<400> SEQUENCE: 27
000

<210> SEQ ID NO 28
<400> SEQUENCE: 28
000

<210> SEQ ID NO 29
<400> SEQUENCE: 29
000

<210> SEQ ID NO 30
<400> SEQUENCE: 30
000

<210> SEQ ID NO 31
<400> SEQUENCE: 31
000

<210> SEQ ID NO 32
<211> LENGTH: 350
<212> TYPE: DNA
<213> ORGANISM: Homo sapiens

<400> SEQUENCE: 32

| | | | | | |
|---|---|---|---|---|---|
| gttgggatgg | tagtgggagg | ggattttttt | ttttaacggg | gttataaaaa | tagcgttttc | 60 |
| ggcggggttt | agtttttttgt | tattttcgtt | tcgaggtttt | cgcgttagag | acgtagtcgc | 120 |
| gttttttatta | tttatattta | tcgcgttttc | gttcgttttt | ttttcgggag | ttagttcgcg | 180 |
| ttatcgtcgt | cgtttaggtt | atcgttattt | ttcgtagtta | tgtttattag | gttcgtgttt | 240 |
| tcgtttttttt | atcgtaggat | gttcggcggt | tcgggtatcg | cgagtcggtc | gagttttagt | 300 |
| cggagttacg | tgattacgtt | tattcgtatt | tatagtttgg | gtagcgcgtt | | 350 |

<210> SEQ ID NO 33
<211> LENGTH: 16
<212> TYPE: DNA

-continued

<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<221> NAME/KEY: modified_base
<222> LOCATION: (4)..(4)
<223> OTHER INFORMATION: Locked nucleic acid
<220> FEATURE:
<221> NAME/KEY: modified_base
<222> LOCATION: (6)..(6)
<223> OTHER INFORMATION: Locked nucleic acid
<220> FEATURE:
<221> NAME/KEY: modified_base
<222> LOCATION: (15)..(15)
<223> OTHER INFORMATION: Locked nucleic acid
<220> FEATURE:
<223> OTHER INFORMATION: 3' BHQ1

<400> SEQUENCE: 33
tttcgcgtta gagacg                                                    16

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tcgttcgagg ttttcgc                                                   17

<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tcgtggtgtg gtgtcgtttc gaggttttcg c                                   31

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gtgtggtgtc gtttcgag                                                  18

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cttcgtggtg tggtgaaaac gcgactacgt ctc                                 33

<210> SEQ ID NO 38
<211> LENGTH: 18

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tgtggtgaaa acgcgact                                                    18

<210> SEQ ID NO 39
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tggtgtggtg cgcgac                                                      16

<210> SEQ ID NO 40
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gctcttcgtg gtgtggtgtt cgtttcgagg ttttcg                                36

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gctcttcgtg gtgtggtgcg cgactacgtc tctaa                                 35

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gtgtggtgtt cgtttcgag                                                   19

<210> SEQ ID NO 43
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tcttcgtggt gtggtgc                                                     17

<210> SEQ ID NO 44
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 44
tggtgtggtg ctccggac                                                    18

<210> SEQ ID NO 45
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gtgtggtgcg gttc                                                        14

<210> SEQ ID NO 46
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gtgtggtgct ccgac                                                       15

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gctcttcgtg gtgtggtgcg gttcgggtat cgc                                   33

<210> SEQ ID NO 48
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gctcttcgtg gtgtggtgct ccgactaaaa ctcgacc                               37

<210> SEQ ID NO 49
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tggtgtggtg cggttc                                                      16

<210> SEQ ID NO 50
<211> LENGTH: 16
<212> TYPE: DNA
<213> ORGANISM: Artificial Sequence
<220> FEATURE:
<223> OTHER INFORMATION: Description of Artificial Sequence: Synthetic
```

```
<210> SEQ ID NO 51
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gtgtggtgcg gtt                                                      13
```